(12) United States Patent
Kozlowski et al.

(10) Patent No.: US 7,094,568 B2
(45) Date of Patent: Aug. 22, 2006

(54) METHOD FOR PRODUCING PROTEINS TAGGED AT THE N- OR C-TERMINUS

(75) Inventors: Roland Kozlowski, Babraham (GB); Michael B. McAndrew, Babraham (GB); Jonathan Michael Blackburn, Cambridge (GB); Michelle Anne Mulder, Capetown (ZA); Mitali Samaddar, Hyderabad (IN)

(73) Assignee: Sense Proteomic Ltd., (GB)

( * ) Notice: Subject to any disclaimer, the term of this patent is extended or adjusted under 35 U.S.C. 154(b) by 477 days.

(21) Appl. No.: 10/114,334

(22) Filed: Apr. 3, 2002

(65) Prior Publication Data

US 2003/0073811 A1 Apr. 17, 2003

Related U.S. Application Data

(63) Continuation-in-part of application No. PCT/GB01/03693, filed on Aug. 17, 2001.

(60) Provisional application No. 60/247,995, filed on Nov. 14, 2000.

(51) Int. Cl.
| | |
|---|---|
| C12P 21/06 | (2006.01) |
| C12N 15/00 | (2006.01) |
| C07K 1/00 | (2006.01) |
| C07H 21/02 | (2006.01) |
| C07H 21/00 | (2006.01) |

(52) U.S. Cl. ............... 435/69.1; 435/91.1; 435/320.1; 530/350; 536/23.1; 536/25.3; 536/25.32

(58) Field of Classification Search .............. 435/69.1, 435/91.1, 320.1; 530/350; 536/23.1, 25.3, 536/25.32
See application file for complete search history.

(56) References Cited

U.S. PATENT DOCUMENTS

| | | | |
|---|---|---|---|
| 6,087,103 A | 7/2000 | Burmer | |
| 6,239,209 B1 | 5/2001 | Yang et al. | |
| 2002/0162622 A1* | 11/2002 | Gut | 156/233 |

FOREIGN PATENT DOCUMENTS

| | | |
|---|---|---|
| WO | WO 99/11777 A1 | 3/1999 |
| WO | WO 99/39210 A1 | 8/1999 |
| WO | WO 99/51773 A1 | 10/1999 |
| WO | WO 00/04382 A1 | 1/2000 |
| WO | WO 00/09654 A2 | 2/2000 |
| WO | WO 00/09654 A3 | 6/2000 |
| WO | WO 01/04265 A2 | 1/2001 |
| WO | WO 01/04265 A3 | 4/2001 |
| WO | WO 01/57198 A2 | 8/2001 |
| WO | WO 01/57198 A3 | 2/2002 |

OTHER PUBLICATIONS

Bordini, E., and Hamdan, M., "Investigation of Some Covalent and Noncovalent Complexes by Matrix-assisted Laser Desorption/Ionization Time-of-flight and Electrospray Mass Spectrometry," *Rapid Commun. Mass Spectrom.* 13:1143-1151, John Wiley & Sons, Ltd. (1999).

Cai, J., et al., "Functional Expression of Multidrug Resistance Protein 1 in *Pichia pastoris*," Biochemistry 40:8307-8316, American Chemical Society (Jun. 2001).

DeRisi, J., et al., "Use of a cDNA microarray to analyse gene expression patterns in human cancer," *Nat. Genet.* 14:457-460, Nature Publishing Co. (1996).

Doellgast, G.J., et al., "Sensitive Enzyme-Linked Immunosorbent Assay for Detection of Clostridium botulinum Neurotoxins A, B, and E Using Signal Amplification via Enzyme-Linked Coagulation Assay," *J. Clin. Microbiol.* 31:2402-2409, American Society for Microbiology (1993).

Giuliani, C.D., et al., "Expression of an active recombinant lysine 49 phospholipase $A_2$ myotoxin as a fusion protein in bacteria," *Toxicon* 39:1595-1600, Elsevier Science Ltd. (2001).

Hara, H., et al., "Molecular cloning and functional expression analysis of a cDNA for human hepassocin, a liver-specific protein with hepatocyte mitogenic activity," *Biochim. Biophys. Acta* 1520:45-53, Elsevier Science B.V. (2001).

Rhodes, N., et al., "Expression and Purification of Active Recombinant ATM Protein from Transiently Transfected Mammalian Cells," *Prot. Express. Purif.* 22:462-466, Academic Press, Inc. (Aug. 2001).

Staudinger, J., et al., "Interactions among Vertebrate Helix-Loop-Helix Proteins in Yeast Using the Two-hybrid System," *J. Biol. Chem.* 268:4608-4611, The American Society for Biochemistry and Molecular Biology, Inc. (1993).

Vojtek, A.B., et al., "Mammalian Ras Interacts Directly with the Serine/Threonine Kinase Raf," *Cell* 74:205-214, Cell Press (1993).

Walker, E.A., et al., "Functional Expression, Characterization, and Purification of the Catalytic Domain of Human 11-β-Hydroxysteroid Dehydrogenase Type 1," *J. Biol. Chem.* 276:21343-21350, The American Society for Biochemistry and Molecular Biology, Inc. (2001).

Zwicker, N., et al., "Strep-tag® II for One-Step Affinity Purification of Active bHLHzip Domain of Human c-Myc," *BioTechniques* 27:368-370 and 372-375, Eaton Publishing Co. (1999).

International Search Report for International Patent Application No. PCT/GB01/03693, mailed Nov. 7, 2002.

\* cited by examiner

*Primary Examiner*—Bennett Celsa
*Assistant Examiner*—Mark L. Shibuya
(74) *Attorney, Agent, or Firm*—Ivor R. Elrifi, Esq.; Mintz Levin Cohn Ferris Glovsky and Popeo PC

(57) ABSTRACT

The present invention relates to novel methods of producing proteins in which one or more domains are full length and correctly folded and which are each tagged at either the N- or C-terminus with one or more marker moieties and arrays containing such proteins, as well as the use of such proteins in arrays for rapid screening.

22 Claims, 6 Drawing Sheets

Figure 1:
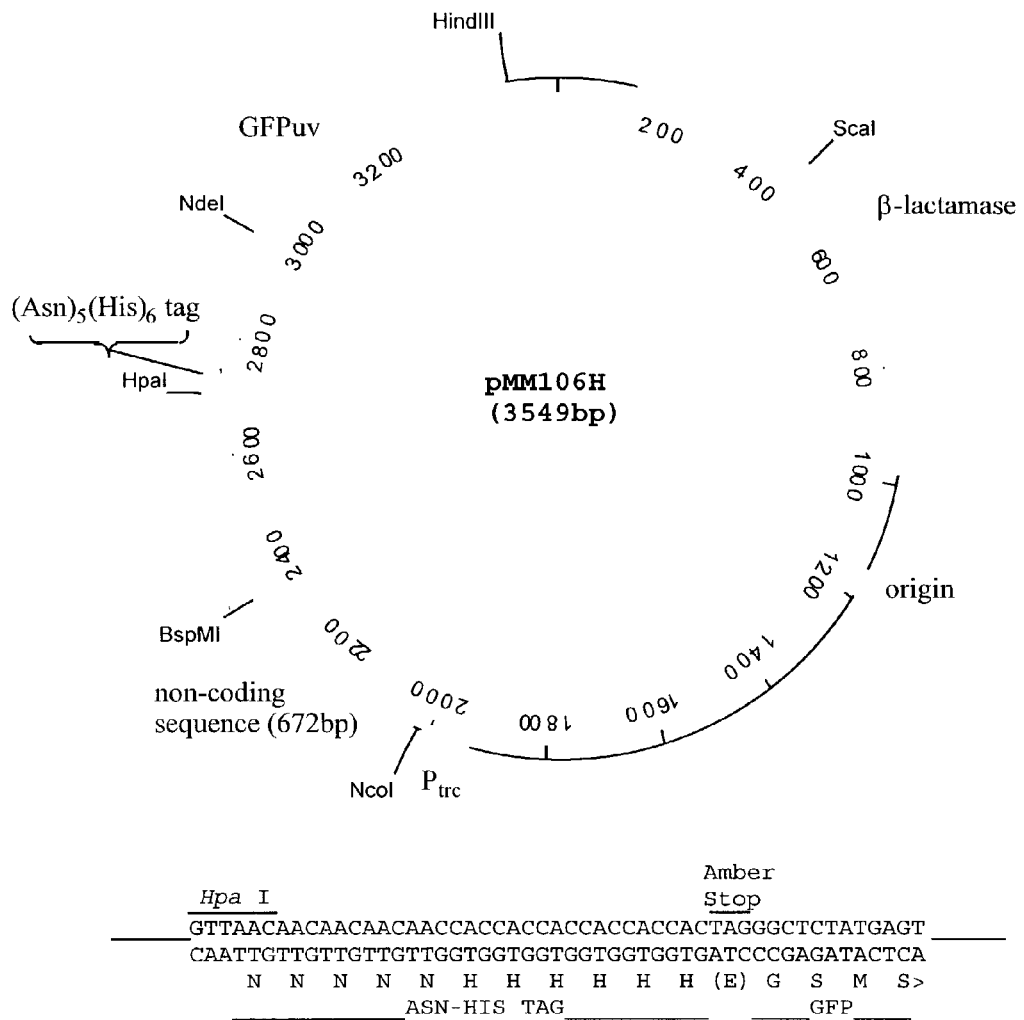

Grow individual colonies in liquid culture and induce expression.

METHOD FOR PRODUCING PROTEINS TAGGED AT THE N- OR C-TERMINUS

CROSS-REFERENCE TO RELATED APPLICATIONS

The present invention is a continuation-in-part of International Application No. PCT/GB01/03693, filed Aug. 17, 2001, and published under PCT Article 21 (2) in English, which claims priority benefit of U.S. Provisional Application No. 60/247,995, filed Nov. 14, 2000 and GB Application No. 0020357.0, filed Aug. 17, 2000, each of which is incorporated by reference in their entirety.

BACKGROUND OF THE INVENTION

1. Field of the Invention

The present invention relates to novel methods of producing proteins in which one or more domains are full length and correctly folded and which are each tagged at either the N- or C-terminus with one or more marker moieties and arrays containing such proteins, as well as the use of such arrays in rapid screening.

2. Related Art

The genome mapping projects are revolutionizing the therapeutic target discovery process and with it the drug discovery process. As new therapeutic targets are identified, high throughput screening of existing and combinatorial chemical libraries will suggest many potential lead compounds which are active against these targets. It will clearly be uneconomic to pursue all lead compounds through even early phase clinical trials; currently however no rapid method exists for evaluating such lead compounds in terms of their likely activity profiles against all proteins in an organism. If available, such a method would allow the potential toxicology profiles of all the lead compounds to be assessed at an early stage and this information would significantly enhance the process of deciding which lead compounds to pursue and which to set aside.

There is a complementary need in the pharmaceutical industry to identify all the targets of existing drugs (either in the market already or still in development) and hence to define their mechanism of action. The availability of such information will greatly facilitate the process of gaining regulatory approval for new drugs since it is increasingly clear that the regulatory bodies now regard a knowledge of the mechanism of action to be of paramount importance. In addition, this type of information would enable the design of improved second generation drugs. This follows because the majority of drugs have at least minor side effects, which probably result from binding of the drug or a metabolite thereof to undesirable targets; all of these target proteins need to be identified in order to define the criteria necessary for design of improved drugs. Currently however no simple method exists to generate this information and a number of potential multi-million dollar drugs fall by the wayside simply for lack of knowledge of the target of action.

Protein-protein interactions are being increasingly recognized as being of critical importance in governing cellular responses to both internal and external stresses. Specific protein-protein interactions therefore represent potential targets for drug-mediated intervention in infections and other disease states. Currently the yeast two-hybrid assay is the only reliable method for assessing protein-protein interactions but in vivo assays of this type will not be readily compatible even in a non-high throughput format with the identification of specific agonists or antagonists of protein-protein interactions. Functional proteome expression arrays, or "proteome chips", will enable the specificity of protein-protein interactions and the specificity of any drug-mediated effect to be determined in an in vitro format. They will therefore have enormous potential because they will simply revolutionize this area of research.

One way in which functional proteome arrays could be generated is to individually clone, express, purify and immobilize all proteins expressed in the specific proteome. Here though, an important initial consideration concerns the absolute size of the genome of interest together with considerations about the availability of sequence data for the entire genome.

By way of illustration of these points, a typical bacterial genome is ~5 Mbp and a small number have now been completely sequenced (for example *Helicobacter pylori*, *Escherichia coli*, and *Mycobacterium tuberculosis*); fungal genomes are typically ~40 Mbp, mammalian genomes at ~3 Gbp and plant genomes at ~10 Gbp. Current estimates are that the human genome sequence will be finished around 2003, although how much of this information will be in the public domain is very much open to question. Clearly it will be completely impractical to expect that the genomes of anything other than representative model organisms will become available in a realistic time frame, yet from the perspective of functional proteomics, model organisms are of only limited value. So, whilst in principle within the next four years it may be possible to design and synthesize primers to clone each of the ~100,000 genes in the human genome from cDNA libraries, in practice this will be both enormously expensive (the cost of primers alone would run in to several millions of dollars) and a hugely laborious process, even if the necessary sequence data is available.

But what about those pharmaceutically relevant organisms for which the complete sequence data will not be available? These cannot be simply ignored by functional proteomics so what are the alternatives? Expression cDNA libraries could in principle be used together with non-specific immobilization to create an array of proteins, but this technology is significantly limited by the fact that non-specific immobilization is usually associated with loss of function because the fold of the protein is disrupted. In addition, all host cell proteins will also be immobilized which will at best markedly reduce signal-to-noise ratios and at worst result in obfuscation of positive results. The ability to create a functional proteome array in which individual proteins are specifically immobilized and purified via a common motif or tag without affecting function and without requiring knowledge of the entire genome sequence would therefore represent a huge advance in the field of functional proteomics.

SUMMARY OF THE INVENTION

The Inventors have now developed a novel approach which solves the problems described above by providing methodology which allows each protein in a proteome to be tagged with a common marker at a defined position within the protein without requiring any prior knowledge of the DNA sequence of the corresponding genes. This 'tag' can then be used to impart a commonality and specificity to downstream immobilization and purification procedures, which in turn enables the creation of spatially defined arrays in which many thousands of proteins from a given proteome are displayed.

An important consideration here relates to the precise positioning of the 'tag'. If the tag is inserted in-frame in to any gene at an undefined, random position, the likelihood is that the resultant tagged protein will be truncated in an undefined manner and in the majority of cases correct folding, and hence function, will be destroyed. It is often found that full-length proteins have short polypeptide extensions at either (or both) the N- and C-termini which can be truncated without affecting folding or function. However, if the truncations remove any N- or C-terminal extensions and cross a domain boundary, folding and function of the protein are usually then compromised. The methodology described here allows the tag to be inserted in the correct reading frame either precisely at the N- or C-terminus of each protein, or within a region close to either terminus which is unimportant in the folding and function of the protein, such that the individual tagged proteins fold correctly and hence retain function when specifically immobilized in the array. In the case of multidomain proteins where individual domains have discrete functions, the methodology described here also allows insertion of the tag within the overall coding sequence but outside specific domain boundaries such that the individual tagged domains fold correctly and hence retain function when specifically immobilized in the array.

Since each protein in the array will be fully functional, the arrays can then be screened directly to identify the targets of drugs and other biologically relevant molecules. The spatial definition of the arrays will allow the phenotype of each protein to be related directly to its genotype to allow the identification of 'hits'.

Thus, in a first aspect, the present invention provides a method producing one or more proteins in which one or more domains are full length and correctly folded and which are each tagged at either the N- or C-terminus with one or more marker moieties, said method comprising:

(a) providing one or more DNA molecules having an open reading frame encoding said proteins together with 5' and/or 3' untranslated regions;

(b) amplifying said DNA molecules under conditions that statistically incorporate α-S-dNTPs as well as dNTPs into the daughter DNA molecules;

(c) specifically protecting the 5' or 3' end of said DNA molecules from nuclease digestion;

(d) treating said DNA molecules first with a 5' to 3'- or 3' to 5'-nuclease to generate a set of nested deletions followed by treating with a single-strand nuclease under conditions that allow removal of said 5' or 3' untranslated regions including the start or stop codons of said open reading frame;

(e) cloning the fragments generated by step (d) into an expression vector containing a coding sequence for one or more 5' or 3' marker moieties; and (f) expressing said encoded proteins.

Preferably the amplification of the DNA molecule or molecules statistically incorporates a single α-S-dNTP, more preferably either α-S-dTTP or α-S-dATP.

The marker moiety can be either a peptide sequence, e.g. a hexa-histidine tag, an antibody epitope or a biotin mimic, or indeed a complete protein, or protein domain, e.g. the maltose binding protein domain. The marker moiety itself can be post-translationally modified, e.g. by addition of a biotin or lipid molecule. In a preferred embodiment, the marker moiety would also allow purification of "tagged" proteins.

Thus, the methods of the present invention allow the specific modification, in one pot, of every member of a cDNA library in a manner which does not rely on any knowledge of the sequence of individual genes. Instead, it relies on non-processive truncation of each cDNA by a nuclease such that either the 5'- or the 3'- untranslated region of each cDNA is removed. Additional known DNA sequence encoding a known marker moiety is then appended to the resultant set of nested deletions of each cDNA. If the marker moiety is in the same reading frame as the individual cDNA and is not preceded by any in-frame stop codon, each resultant genetically modified cDNA produced according to the methods of the present invention will thus encode an individual protein which now has a common moiety, e.g. a polypeptide "tag" fused to either its N- or C-terminus. A screen for correctly folded, tagged proteins then allows all truncations which cross a domain boundary and affect the folding (and hence function) of the individual protein and all out-of-frame fusions to the tag to be discarded.

Since every member of a cDNA library will be modified in the same manner, the net result will be that every protein encoded by the cDNA library will now be tagged with a common moiety at either their N- or C-termini.

In general, the proteins expressed from the cDNA library will be "tagged" and can be readily identified and isolated. Once purified they can be attached to microarrays, for example. Attachment can be effected by means of the tag itself, or alternatively, by means of another moiety which is first attached to the proteins.

In a variation of the first aspect of the invention and as described in Example 1(d) and Example 5, the invention also provides a method for producing one or more proteins in which one or more domains are full length and correctly folded and which are each tagged at either the N- or C-terminus with one or more marker moieties, said method comprising:

(a) providing one or more DNA molecules having an open reading frame encoding said proteins together with 5' and/or 3' untranslated regions;

(b) treating said DNA molecules first with a 5' to 3'- or 3' to 5'-nuclease to generate a set of nested deletions followed by converting the nested set of deletions into blunt-ended double stranded DNA molecules;

(c) cloning the fragments generated by step (b) into an expression vector containing a coding sequence for one or more 5' or 3' marker moieties; and (d) expressing said encoded proteins.

It will be apparent to a person skilled in the art that various methods exist for the conversion of the nested set of deletions of step (b) into blunt-ended double stranded DNA molecules. A particularly preferred method generates or produces the blunt-ended double stranded DNA molecules by treating the set of nested deletions with a single-strand nuclease under conditions that allow removal of said 5' or 3' untranslated regions including the start or stop codons of said open reading frame. For example step (b) can be carried out under conditions which vary the concentration of sodium chloride, the temperature and/or the amount of nuclease present to control activity of the exonuclease and/or which vary the time at which nuclease activity is quenched. It will be understood by those skilled in the art that whilst for a subset of the population of nested deletions, the single-strand nuclease will remove the 5' or 3' untranslated regions including the start or stop codons of the open reading frame, for the whole population, the single-strand nuclease will remove the exposed single-strand overhangs generated by the 5' to 3'- or 3' to 5'-nuclease but may not necessarily remove the whole 5' or 3' untranslated regions including the start or stop codons for every member of that population.

The source of the DNA molecules of step (a) can, for example, be double stranded cDNA synthesis products. "Double stranded cDNA synthesis products" are defined herein as those double stranded DNA molecules obtained by providing one or more mRNA molecules, reverse transcribing said mRNA molecules to produce first strand cDNA and then synthesizing complementary second strand DNA molecules using a DNA polymerase to produce duplex DNA. The use of such molecules in an un-cloned state (i.e. not part of a plasmid, cosmid or other DNA vector) has the advantage of reducing any bias that might exist between different coding sequences within a library produced from an mRNA sample, for example during growth of vectors containing the cloned molecule in culture. This is further described in Example 6 herein.

As an optional step after step (a) and prior to step (b) of the method of this aspect of the invention, the DNA molecules are specifically protected at the 5' or 3' end from nuclease digestion as described herein.

The DNA molecules of step (a) can be biotinylated by methods known in the art to facilitate identification or separation of the molecules. Biotin groups can be conveniently positioned at the 5' end of one strand, for example by way of reverse transcriptase extended primers. In any case, biotin groups should be positioned such that they are not removed by step (b).

Optionally the method of this aspect of the invention can be carried out at step (a) upon DNA molecules provided as linearised plasmids. Such plasmids can, for example be derived from a cDNA library, for example, plasmids obtained by propagating bacterial cells containing a cDNA library through growth of individual cultures each containing a single clonal member of the library.

In a further aspect of the invention, an array of proteins is provided in which one or more domains are full length and correctly folded and which are tagged at the C-terminus with one or more marker moieties, said marker moieties being appended to the encoding DNA molecules in a sequence independent manner. Such arrays can be constructed, for example from a cDNA library, by the methods described herein.

Arrays formed by the methods described herein form a second aspect of the invention. In general, an "array" is an arrangement of entities in a pattern on a substrate. The pattern can be a two-dimensional or a three dimensional pattern, and the distance separating the entities can vary. The number of different entities on the array will vary depending on the application desired.

Such arrays comprise the "tagged" protein expression library, immobilized, usually on a solid support. The terms "substrate" and "solid support" typically denote a material having a rigid or semi-rigid surface, e.g., a membrane, a microtiter dish, etc. For example, by a "solid support" is meant, without limitation, any column (or column material), bead, test tube, microtiter dish, solid particle (for example, agarose or sepharose), microchip (for example, silicon, silicon-glass, or gold chip) or membrane (for example, the membrane of a liposome or vesicle). The purpose of the substrate/solid support is to use spatial positioning of an array to allow identification of the individual proteins. The skilled person will understand that a range of possible solid supports are in common usage in the area of arrays and any of these "substrates" can be utilized in the production of arrays of the present invention. See, e.g., U.S. Pat. Nos. 6,329,209 and 6,087,103.

As discussed herein the term "protein array" relates to a spatially defined arrangement, as commonly understood by one of skill in the art, of one or more protein moieties in a pattern on a surface, for example, in a matrix such as a microtiter dish, so that each well of the dish has a single library member. Preferably the protein moieties will be attached to the surface either directly or indirectly. The attachment can be non-specific (e.g. by physical absorption onto the surface or by formation of a non-specific covalent interaction). In a preferred embodiment the protein moieties will be attached to the surface through the common marker moiety linked to each protein using the methods described herein.

As used herein, the term "protein" means a polymer of amino acid residues linked together by peptide bonds. The term refers to proteins, polypeptides, and peptides of any size, structure or function. Typically, however, a protein will be at least six amino acids long. A protein may be naturally occurring, recombinant or synthetic, or any combination of these.

In another embodiment, the protein moieties may be incorporated into a vesicle or liposome which is tethered to the surface.

Thus, for example, each position in the pattern may contain one or more copies of:

(a) a sample of a single protein type (in the form of a monomer, dimer, trimer, tetramer or higher multimer);

(b) a sample of a single protein type bound to an interacting molecule (e.g. DNA, antibody, other protein);

(c) a sample of a single protein type bound to a synthetic molecule (e.g. peptide, chemical compound); or (d) mixtures of between 2 and 100 different tagged protein moieties at each position in the pattern of the array.

The surface which supports the array may be coated/derivatised by chemical treatment, for instance. Examples of suitable surfaces include glass slides, polypropylene or polystyrene, silica, gold or metal support or membranes made of, for example, nitrocellulose, PVDF, nylon or phosphocellulose.

As discussed herein, the methods of the present invention allow tagging of all proteins in a given proteome specifically at either the N- or C-terminus. Whilst some proteins may not tolerate N-terminal extensions and others might not tolerate C-terminal extensions, it is likely that the vast majority of proteins will tolerate one or other such extensions. Existing library cloning methods, however, simply cannot address this problem since they clone genes either as full-length, unmodified cDNAs or as random and almost inevitably truncated fusions to some protein partner. Compared to the latter, the present methods allow the position of the tag to be targeted to the sequences at or close to the N- or C-terminal residues of the cDNA products such that fusion to e.g. a desired peptide partner does not affect folding or function of the cDNA product. Compared to the former, the method of immobilizing proteins in an array as described herein is through specific rather than non-specific interactions, and these specific interactions are a function of the tag added to the termini of each cDNA. Additionally, the methods described herein can be used to screen purified, immobilized proteins which have been expressed in non-bacterial host organisms to aid maintenance of function through correct folding and post-translational modification, whereas existing methods such as phage display or λ-cDNA expression libraries are restricted to bacterial hosts in which the majority of eukaryotic proteins are found to be synthesized in a non-functional form, either due to mis-folding or incorrect post-translational modification.

The methods of the present invention have a wide range of potential in vitro applications, which can be broadly divided into three main areas. These are the study of protein-ligand interactions, the study of protein-protein interactions, and the study of protein-DNA interactions.

Protein-Ligand Interactions.

The methods described herein will allow the rapid profiling of the interactions between a given new chemical entity and all proteins in a given proteome. This can be achieved simply through probing the appropriate proteome array with the NCE at varying stringencies in what might be considered a reverse high throughput screen. The readout from such a screen will be directly useful in many situations, some of which are described below.

High throughput screening programs in which libraries of compounds are tested against cells or whole organisms often identifies leads, which give rise to a phenotypic change without the target being known prior to screening. Subsequent identification of the primary target can, however, be a very laborious process. The methods of the present invention can be applied directly to this type of problem since it will be possible to create a functional proteome array for the species concerned and then screen this array with the lead compound to identify which proteins within the proteome it is targeting. This massively parallel approach to identifying protein-ligand interactions will greatly speed up and simplify the determination of primary targets of NCEs, and will also allow identification of weaker secondary interactions which may also be important. In addition, the methods can be applied directly to the question of species cross-reactivity, allowing a potential antifungal compound, for example, to be quickly assessed in terms of its interactions with, for example, all proteins in a human proteome; this type of information is likely to prove very useful in any subsequent optimization of lead compounds.

High throughput screening methods now allow the rapid identification of small molecules which bind to a given protein which has itself previously been identified as a potential therapeutic target. However, these methods do not address the question of how selective any given interaction might be yet this knowledge is potentially crucial in deciding whether to pursue a given lead compound or not; perceived wisdom would argue that compounds which target single proteins are likely to show fewer side effects than those which also hit a large number of related or unrelated proteins.

There are a number of examples of compounds which have progressed successfully through third phase clinical trials yet have failed to win regulatory approval because their primary mechanism of action is not known. The antidepressant drugs mianserin and trazadone and the Pfizer anti-arthritic drug tenidap are examples here, each representing hundreds of millions of dollars investment for no return. The methods described herein can potentially be applied to the resurrection of such failed drugs since if the primary targets of such drugs can be discovered and subsequently verified in terms of mechanism of action, the vastly expensive clinical trial data is already in place for regulatory approval.

All existing drugs have side effects, to a greater or lesser extent, an example here being the otherwise attractive anti-schizophrenia drug clozapine. If the molecular origin of such side effects could be determined, this would greatly facilitate the design of future generation drugs with optimized primary effects combined with minimized side effects. Again the presently described methods can be applied directly to such problems since in creating a profile of the interactions between a compound and all proteins in a proteome, aberrant secondary interactions will be identified and these can subsequently be assessed in terms of whether they are linked to known side effects.

The methods of the present invention can also be used to identify families of proteins, such as serine proteases, through screening proteome arrays with generic inhibitors. This would then allow the subsequent development of biochips displaying, for example, all human serine proteases or, alternately, all kinases or all p450 enzymes for more focused screening of lead compounds. A p450 biochip, for example, would have utility in assessing whether a given lead compound is likely to be metabolized or not, since p450-mediated hydroxylation is often the first step in this process and is thought to be one of the primary sources of patient-to-patient variability in drug response; indeed one of the goals of drug design now is to generate compounds which are not metabolized in the first place and here again a p450 chip would have significant potential utility.

Protein-Protein Interactions.

Protein-protein interactions and multiprotein complexes are of critical importance in cellular biology. Signaling pathways, for example, are commonly initiated by an interaction between a cell surface receptor and an external ligand, and this is followed by a cascade of protein-protein interactions which ultimately result in the activation of a specific gene. Individual protein-protein interactions might be dependent on the presence of a specific ligand or alternatively might be blocked by a specific ligand, whilst some multiprotein complexes will only form in a ligand-dependent manner.

Thousands of new protein-protein interactions have been identified using two-hybrid technologies. The methods described herein overcome the limitations of such methods and can be used to screen proteome arrays with individual labeled proteins to identify not only interacting partners but also the relative strengths of individual interactions. The methods can also be applied to the identification of the components of multiprotein complexes, even where their assembly is ligand dependent.

An example of the use of the methods in this way in defining novel protein-protein interactions would be the identification of the signaling partners of the cytosolic domain of a particular cell surface receptor which has been implicated in a disease state; identification of such signaling partners would be directly relevant from a pharmaceutical perspective since such protein-protein interactions might immediately represent possible therapeutic targets.

Protein-DNA Interactions.

It has been estimated that roughly 10% of all genes in the human genome encode transcription factors yet only a small percentage of these are at present identified. The binding of specific transcription factors to DNA enhancer elements, often in response to external stimuli, is a prerequisite for the formation of enhanceosome complexes which then switch on gene expression. There are various points at which gene expression can in principle be affected by drug administration: a drug might block the binding of a protein or small molecule to a cell surface receptor and hence block the signaling cascade at the beginning; a drug might block a protein-protein interaction or inhibit an enzymatic activity within the signaling cascade; or alternatively, a drug might block formation of specific protein-DNA or protein-protein interactions within the enhanceosome complex. As an example here, the transcription factor NF-κB is involved in cellular processes as diverse as immune and inflammation responses, limb development, septic shock, asthma, and HIV propeptide production. The majority of the intracellular signaling cascades in NF-κB activation are common to all these process so do not represent viable targets for intervention. The differences between the responses therefore lie in either the original ligand-receptor interaction or in the formation of specific enhanceosome complexes. NF-κB is known to bind to at least 14 different enhancer elements and the enhanceosome complexes therefore represent potential therapeutic targets. However, delineation of an individual enhanceosome complex requires knowledge of both the number of individual DNA-binding proteins involved and also their protein-protein interactions with each other. The present methods can be used to directly address both these questions. A proteome array can be screened with specific DNA probes to identify novel DNA binding proteins. Alternatively, the proteome array can be screened with the transactivation domain of a given transcription factor to identify other proteins with which it interacts. Cross correlation of such screens should allow identification of new components of specific enhanceosome complexes.

The protein arrays generated by the methods of the present invention will also allow the selection of molecules which recognize each protein displayed in the arrays. In a preferred embodiment, the selected molecules will be antibodies or antibody-like proteins and will be displayed on phage or on ribosomes or will be covalently linked to the encoding mRNA.

Thus, a phage displayed antibody library can be applied to each immobilized protein in the array and non-binding antibodies removed by washing. The selected phage can then be recovered and used to infect bacteria according to normal procedures. The phage-infected bacteria can then produce either phage particles displaying the selected antibodies for further rounds of selection, or they can produce soluble antibody fragments for direct use. The terms 'antibody' or 'antibody fragments' here refer to single chain Fvs, FAB fragments, individual light or heavy chain fragments, derived from mouse, human, camel or other organisms.

In a preferred embodiment, the protein array will be in microwell format such that after the selection step, the phage particles can be recovered by addition of appropriate bacterial cells to each well where they will become infected by the selected phage particles. Growth media can then be added to each well and the infected bacteria allowed to grow and express the antibody fragments, whilst maintaining the physical separation of the antibody fragments selected to each immobilized protein in the array. If so desired, new phage particles produced by the infected bacteria can be used in subsequent rounds of selection. Such procedures are now routine for selecting polyclonal or monoclonal antibody fragments to a single purified and immobilized protein. In effect then the original protein arrays here will allow the generation of polyclonal or monoclonal antibody fragments to thousands of correctly folded proteins in a massively parallel manner whilst otherwise using standard in vitro antibody selection methods.

The selected, solubly expressed antibody fragments from each well of the original array can themselves be immobilized in to a new spatially defined array such that the antibody fragments in each position of the new array were selected against the proteins immobilized in a single, defined position in the original array. The antibody arrays so-generated will contain at each position either polyclonal or monoclonal antibody fragments, depending on the number of rounds of selection carried out prior to immobilization of the soluble antibody fragments.

Such antibody arrays will have a number of potential uses including capture of individual proteins from a crude cell or tissue lysate for differential expression monitoring of the relevant proteome. Alternatively, the antibody-captured proteins might be screened directly for ligand-binding function. In general, any one monoclonal antibody might bind to the target protein so as to block its function, but another monoclonal antibody might bind but not block function. In a massively parallel approach, it is clearly impractical to assess all monoclonal antibodies to all proteins in a proteome individually for their ability to bind but not affect function. A polyclonal set of antibodies to all proteins in a proteome however is likely to contain individual antibodies which have the desired ability to bind but not affect function and will, in addition, contain individual antibodies which recognize all post-translational modifications of a given protein. Thus in general, polyclonal rather than monoclonal antibody arrays generated as described will likely be advantageous for screening captured proteins directly for function.

Compared to the original protein arrays, the antibody arrays created by the methods described here will have the advantage that all proteins immobilized on the array will be stable under similar conditions. The proteins captured from the crude cell or tissue lysate will not be recombinant but will have been naturally expressed. Moreover, the captured proteins can be screened for function or ligand binding etc. directly after capture from the crude cell or tissue lysate, which should aid maintenance of function.

Thus, in further aspects, the present invention provides:

(i) a method of screening one or more compounds for biological activity which comprises the step of bringing said one or more compounds into contact with a protein array as defined herein and measuring binding of the one or more compounds to the proteins in the array;

(ii) a method of screening one or more proteins for specific protein-protein interactions which comprises the step of bringing said one or more proteins, e.g. a cell surface receptor, into contact with an array as defined herein, and measuring binding of the one or more specific proteins with the proteins of the array;

(iii) a method of screening one or more proteins for specific protein-nucleic acid interactions which comprises the step of bringing said one or more nucleic acid probes into contact with an array as defined herein and measuring binding of the probes to the proteins in the array;

(iv) the use of an array as defined herein in the rapid screening of a compound, protein or nucleic acid;

(v) the use of an array as defined herein in screening for molecules which recognize each protein in the array, wherein the molecules are preferably antibodies;

(vi) a method of generating an antibody array which comprises bringing a protein array, as defined herein, into contact with an antibody library, such that one or more proteins in the protein array bind to at least one antibody in the antibody library, removing any unbound antibodies and immobilization of those antibodies bound to proteins in the protein array; and (vii) a method for the screening of protein function or abundance which comprises the step of bringing an antibody array as defined herein into contact with a mixture of one or more proteins.

The methods (i), (ii), (iii) and (vi) may also include the step of first providing the array according to one or more of the methods of the present invention.

Use of the proteins derived from the methods described herein form additional aspects of the invention. The skilled person will understand that a range of applications are known in the art in which modified proteins may be employed.

Thus, in further aspects, the present invention provides:

(i) the expression of tagged proteins produced by the methods of the invention in numerous expression hosts i.e. bacteria, yeast, mammalian cells (for example see, Walker E A, Clark A M, Hewison M, Ride J P, Stewart P M. Functional expression, characterization, and purification of the catalytic domain of human 11-beta -hydroxysteroid dehydrogenase type 1. J Biol Chem 2001 Jun. 15;276(24):21343–50; Cai J, Daoud R, Georges E, Gros P. Functional Expression of Multidrug Resistance Protein 1 in *Pichia pastoris*. Biochemistry 2001 Jul. 17;40(28):8307–16, and Hara H, Yoshimura H, Uchida S, Toyoda Y, Aoki M, Sakai Y, Morimoto S, Shiokawa K. Molecular cloning and functional expression analysis of a cDNA for human hepassocin, a liver-specific protein with hepatocyte mitogenic activity. Biochim Biophys Acta 2001 Jul. 30;1520(1):45–53);

(ii) the use of a tagged protein produced by the methods as defined herein;

(iii) the use of a tagged protein produced by the methods as defined herein for analysis of interaction between expressed protein and other proteins within a yeast two-hybrid system via the cloning of said modified DNA molecule into a yeast two-hybrid expression vector (for example see, Staudinger J, Perry M, Elledge S J, Olson EN. Interactions among vertebrate helix-loop-helix proteins in yeast using the two-hybrid system. J Biol Chem 1993 Mar. 5;268(7):4608–11, and Vojtek A B, Hollenberg S M, Cooper J A. Mammalian Ras interacts directly with the serine/threonine kinase Raf. Cell 1993 Jul. 16;74(1):205–14);

(iv) the use of a tagged protein produced by the methods as defined herein for immobilization on an affinity column/substrate, for example to allow the purification by affinity chromatography of, for example, a) interacting proteins, b) DNA or c) chemical compounds. (for example see, Rhodes N, Gilmer T M, Lansing T J. Expression and purification of active recombinant atm protein from transiently transfected mammalian cells. Protein Expr Purif 2001 August;22(3): 462–6; Zwicker N, Adelhelm K, Thiericke R, Grabley S, Hanel F. Strep-tag II for one-step affinity purification of active bHLHzip domain of human c-Myc. Biotechniques 1999 August;27(2):368–75, and Giuliani C D, Iemma M R, Bondioli A C, Souza D H, Ferreira L L, Amaral A C, Salvini T F, Selistre-de-Araujo H S. Expression of an active recombinant lysine 49 phospholipase A(2) myotoxin as a fusion protein in bacteria. Toxicon 2001 October;39(10): 1595–600);

(v) the use of a tagged protein produced by the methods as defined herein in the immobilization by affinity purification for interrogation by antibodies (ELISA assay) as a diagnostic tool (for example see, Doellgast G J, Triscott M X, Beard G A, Bottoms J D, Cheng T, Roh B H, Roman M G, Hall P A, Brown J E. Sensitive enzyme-linked immunosorbent assay for detection of *Clostridium botulinum* neurotoxins A, B, and E using signal amplification via enzyme-linked coagulation assay. J Clin Microbiol 1993 September;31(9):2402–9);

(vi) the use of a tagged protein produced by the methods as defined herein as a probe for a cDNA microarray to identify DNA binding proteins (for example, see DeRisi J, Penland L, Brown P O, Bittner M L, Meltzer P S, Ray M, Chen Y, Su Y A, Trent J M Use of a cDNA microarray to analyze gene expression patterns in human cancer. Nat Genet 1996 December;14(4):457–60); and (vii) the use of a tagged protein produced by the methods as defined herein for elucidating the identity of proteins in the 'proteome' by mass spectrometric analysis of expressed protein components of source library or start material modified by the methods of the invention (for example, see Bordini E, Hamdan M. Investigation of some covalent and noncovalent complexes by matrix-assisted laser desorption/ionization time-of-flight and electrospray mass spectrometry. Rapid Commun Mass Spectrom 1999;13(12):1143–51).

Preferred features of each aspect of the invention are applicable to each other aspect, mutatis mutandis.

Unless defined otherwise, all technical and scientific terms used herein are intended to have the same meaning as is commonly understood by one of ordinary skill in the relevant art. All patents and publications mentioned herein are expressly incorporated by reference in their entirety.

BRIEF DESCRIPTION OF THE FIGURES

FIG. 1 shows the construction of the vector pMM106H.

FIG. 2 shows details of the PCR amplification and exonuclease digestion of an example gene (GST) prior to tagging.

FIG. 3 shows details of the specific ligation and PCR amplification to introduce the tag.

FIG. 4 shows the reaction between Glutathione and 1-chloro-2,4-dinitrobenzene catalyzed by GST.

FIG. 5 shows the plasmid map of pIFM101-C/stuffer.

FIG. 6 shows an overview of the creation of a library of soluble, folded, C-terminally tagged proteins.

DETAILED DESCRIPTION OF THE INVENTION

The present invention will now be described with reference to the following examples, which should not in any way be construed as limiting the scope of the invention.

EXAMPLE 1

(a) Vector Construction (see FIG. 1).

The Inventors constructed a vector pMM106H derived from pUC19 which contains a strong hybrid promoter (Ptrc) to drive the expression of genes cloned into an Nco I site immediately downstream of the promoter sequence. The Inventors inserted a 676 bp nonsense DNA sequence as a stuffer fragment between the Nco I site and a downstream Hpa I site. Hpa I is a blunt-end cutter and is positioned to cleave the vector such that the downstream DNA encodes a polyasparagine, hexahistidine peptide if the reading frame is on the first base of the blunt-end. Following the hexahistidine tag is an amber stop codon (TAG) followed by the gene encoding the green fluorescent protein (GFP) of the jellyfish *Aequorea victoria*. The construction of pMM106H was confirmed by sequencing.

Genes cloned into pMM106H as Nco I/blunt-end fragments result in fusions to the His-tag and GFP only if the correct reading frame is created at the Hpa I site during cloning. GFP is used here as a reporter gene to facilitate visual screening of clones expressing the His tag, while also providing an indication of the correct folding of the fusion protein, since GFP is only active when folded into the correct conformation. The amber stop codon will result in a small amount of the full length fusion protein for visualization of green colonies, while most of the fusion protein will terminate immediately after the His tag and can be used for subsequent immobilization and enzyme assays. It should be understood that a number of different peptides of proteins, whose soluble expression confers some observable phenotype on the cells, could be used in place of GFP as markers for expression and folding of the tagged proteins. These include, but are not limited to, chloramphenicol acetyl transferase, β-galactosidase, the lacZ fragment of β-galactosidase, and proteins capable of repressing transcription, such as the λ-CI repressor.

The template used in the procedure outlined below was pGSTN. This plasmid was constructed by first PCR-amplifying the Schistosoma japonicum glutathione S transferase (GST) gene from pGEX-2T (Pharmacia) under standard conditions using primers 'GSTfwd2' (5'-ATG CTG CAG ACG TCA ACA GTA TCC ATG GCC CCT ATA CTA GG-3') (SEQ ID NO:1) and 'GSTHindIII' (5'-GCG AGG AAG CTT GTC AAT CAG TCA CGA TGA ATT CCC G-3') (SEQ ID NO:2). These primers introduce an Nco I restriction site at the start codon of GST, mutate the second residue of GST from serine to alanine, and introduce a stop codon in the multiple cloning site 3'- of the GST gene followed by a Hin dIII restriction site. The PCR product was then cloned under standard conditions as an Nco I/Hin dIII fragment into pTrcHisA (Invitrogen) previously digested with Nco I/Hin dIII to generate pGSTN.

Figure 2:
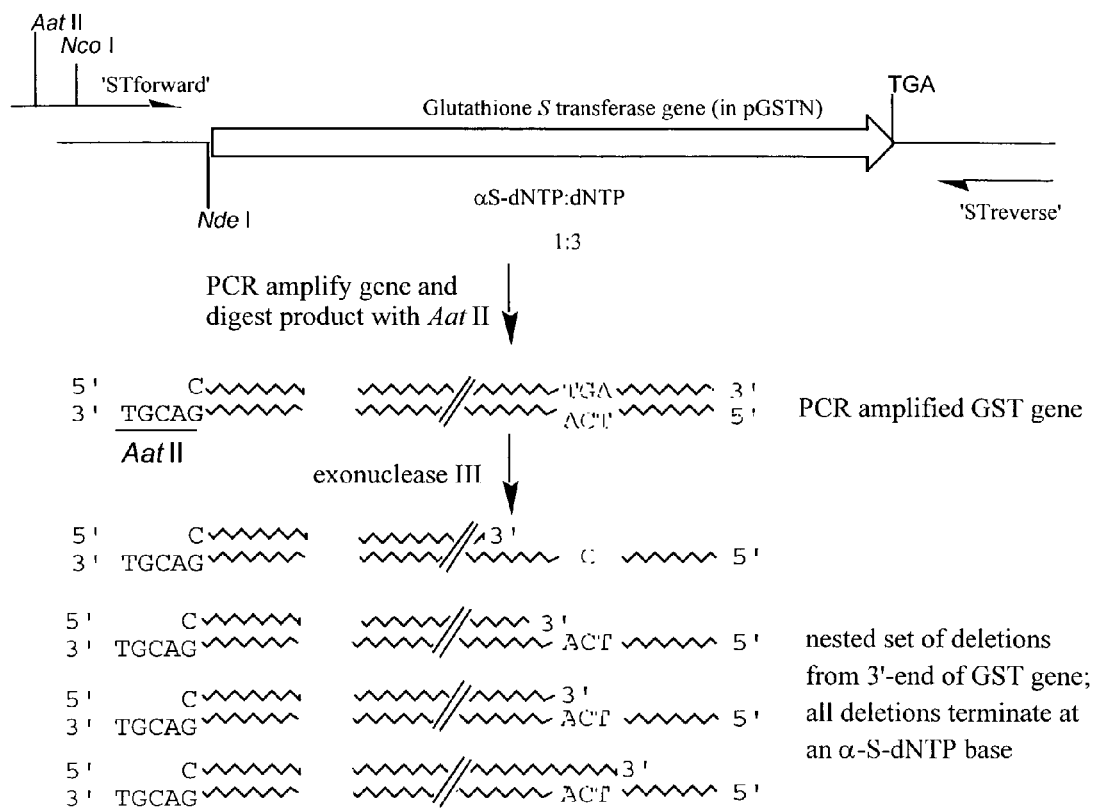

(b) PCR Amplification and Exonuclease Digestion of Genes Prior to Tagging (see FIG. 2).

The Inventors amplified the GST gene from the construct pGSTN using the polymerase chain reaction with custom-designed vector-specific primers 'STforward' (5'-ATG CTG ACG TCA TGA GGC CCA TGG GGC CCG GAT AAC AAT TTC ACA CAG G-3') (SEQ ID NO:3) and 'STreverse' (5'-GCG GAT CCT TGC GGC CGC CAG GCA AAT TCT GTT T-3') (SEQ ID NO:4) which bind to the vector 156 bp upstream of the start and 84 bp downstream of the stop codons respectively. 30 cycles of PCR (94° C. 1 min; 57° C. 1 min; 72° C. 2 min) were carried out in four separate 100 μl reactions. Each PCR reaction contained ~20 ng template DNA, 50 pmol each primer and 2.5 units Pwo polymerase. Each PCR reaction was carried out in a standard buffer (10 mM Tris.HCl pH8.8, 25 mM KCl, 5 mM $(NH_4)_2SO_4$, 2 mM $MgSO_4$, 10% DMSO). Each of the four PCR reactions then also contained a non-standard deoxynucleotide triphosphate mix, as follows:

Reaction 1) 200 μM dATP, 200 μM dTTP, 200 μM dCTP, 150 μM dGTP, 50 μM α-S-dGTP;

Reaction 2) 200 μM dATP, 200 μM dTTP, 200 μM dGTP, 150 μM dCTP, 50 μM α-S-dCTP;

Reaction 3) 200 μM dATP, 200 μM dGTP, 200 μM dCTP, 150 μM dTTP, 50 μM α-S-dTTP;

Reaction 4) 200 μM dGTP, 200 μM dTTP, 200 μM dCTP, 150 μM dATP, 50 μM α-S-dATP.

The amplification of the template DNA in the presence of α-S-dNTPs can of course be carried out by primer extension reactions using many different DNA polymerase, including thermostable polymerases which lack a 3' to 5' exonuclease activity, such as Tap polymerase, and non-thermostable polymerases, such as T4 DNA polymerase or the Klenow fragment of DNA polymerase I.

The inclusion of a single α-thio deoxynucleotide triphosphate in each specific PCR mix results in a random but statistical incorporation of the relevant α-S-dNTP into the specific final PCR product. These modified nucleotides are not substrates for Exonuclease III, and are used to halt the progressive removal of nucleotides by the enzyme. The four individual PCR mixes were then pooled, and purified using a QIAquick PCR cleanup kit (Qiagen), under standard conditions, and digested to completion with the restriction enzyme Aat II. The resulting ~1000 bp PCR products were then gel-purified. Restriction with Aat II results in a 3'-overhang which is resistant to Exonuclease III activity and, therefore, protects the 5' end of the PCR product from degradation.

Alternative methods for specifically protecting one end of the PCR product from exonuclease digestion can be readily envisaged including, but not restricted to the following. Any restriction enzyme which generates a 3'-overhang of 4 bases or more could be used in place of Aat II providing the requisite site is incorporated into the design of the PCR primers. Any restriction enzyme which generates a 5'-overhang could also be used in place of Aat II providing the requisite site is incorporated into the design of the PCR primers; in this case, generation of the 5'-overhang would be followed by a DNA-polymerase-mediated fill-in reaction in which the relevant α-thio dNTPs were used in place of the dNTPs such that the new 3'-end of the PCR product is now protected from exonuclease digestion.

10–15 μg of the digested PCR product was then incubated with 75 units of Exonuclease III/μg of DNA for 30 minutes at 37° C. in a 150 μl reaction. The Exo III digestion was carried out in a standard reaction buffer (66 mM Tris.HCl pH 8.0, 6.6 mM $MgCl_2$, 5 mM DTT, 50 μg/ml bovine serum albumin). These conditions ensure that digestion by Exo III has reached completion. The enzyme was then inactivated by heating to 75° C. for 15 minutes. The product of the Exo III digestion is a nested set of deletions from the 3'-end of the PCR product.

Exonuclease III is a non-processive 3'- to 5'-exonuclease which is unable to hydrolyze α-thio-containing nucleotides so, in the present protocol, every time Exo III reaches an α-thio-deoxynucleotide base, the progressive truncation of the recessed 3'-end of the PCR product is halted. The net result is thus a nested set of deletions as a consequence of the random incorporation of each α-S-dNTP at the earlier stage. The ratio of α-S-dNTP to dNTP used in the original PCR amplifications was determined empirically such that the envelope of nested deletions spanned a 400 bp window of sizes centered approximately 100 bp shorter than the original full length PCR product.

The size range of the truncations obtained can be controlled by altering the ratio of α-S-dNTP to normal dNTP. This is important when the method is applied to eukaryotic cDNAs because such cDNAs have variable length 3' untranslated regions, with the most common 3'-UTR length falling in the range of 200–300 bp. Since the relative efficiency of incorporation of each of the four α-S-dNTPs varies according to the identity of the polymerase, it is desirable to use α-S-dNTP to normal dNTP ratios which are optimized for each of the four bases and for the particular polymerase. Typically, the molar ratio of racemic α-S-dNTP to normal dNTP used will lie in the range 1:1 to 1:3.

Figure 3:
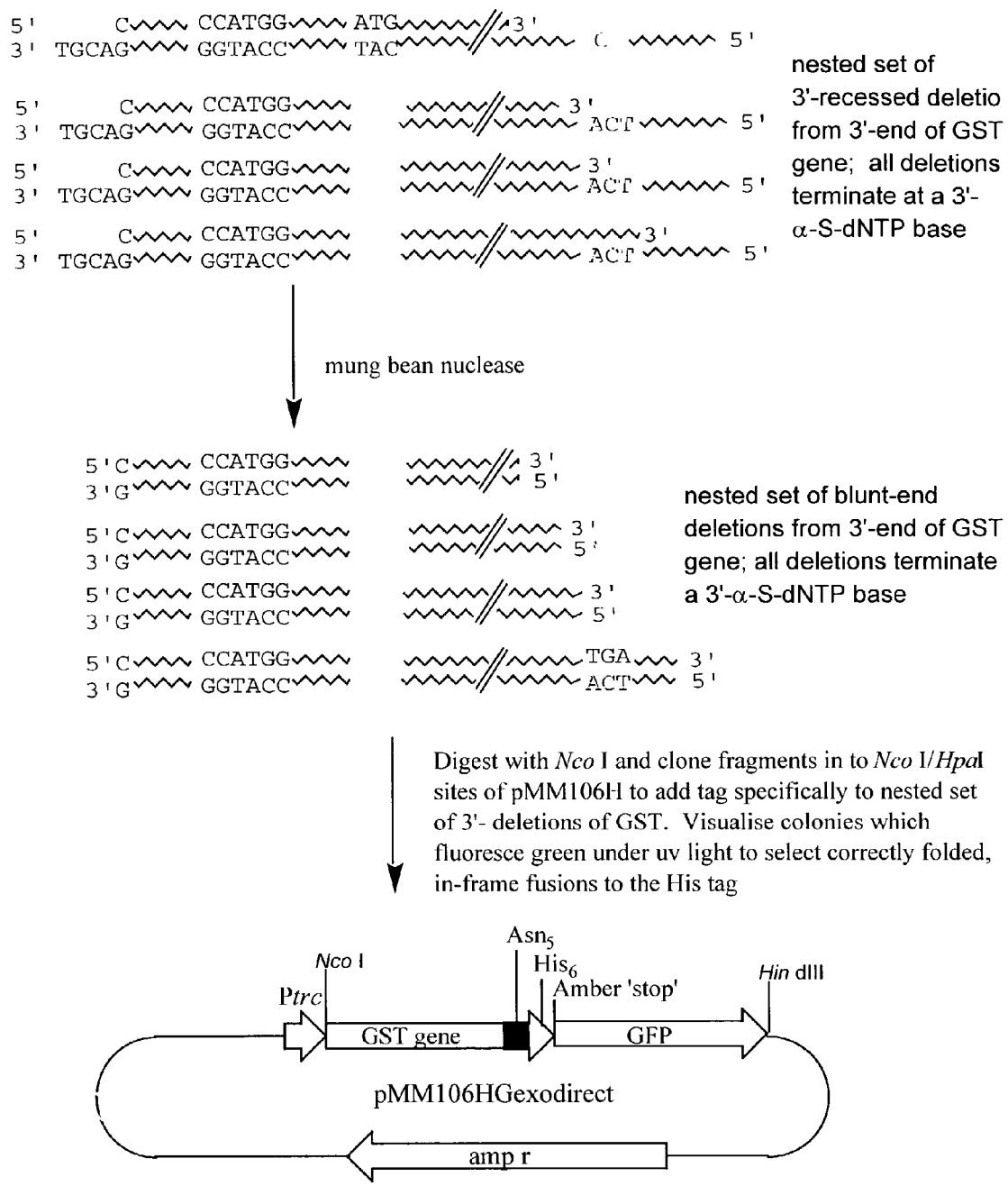

(c) Removal of Single-stranded Regions and Preparation for Cloning (see FIG. 3).

The nested set of deletions generated by Exonuclease III digestion in the previous step was purified by ethanol precipitation and resuspended in 1× mung bean nuclease buffer (50 mM sodium acetate pH5.0, 30 mM NaCl, 1 mM $ZnSO_4$). The digested DNA was treated with (2 units/μg) 30 Units of mung bean nuclease in a 100 μl reaction at 30° C. for 30 minutes. This process removed the 5'- and 3'-overhangs to yield blunt-end products. The reaction was stopped by the addition of EDTA to a final concentration of 5 mM. The digested products were purified using a QIAquick PCR purification kit (Qiagen), digested with Nco I, and separated on a 1% agarose/TBE gel, using a 100 bp DNA ladder as a standard. Products ranging in size from 800 to 1000 bp were extracted from the agarose using a QIAquick gel extraction kit (Qiagen).

Clearly, other single-strand nucleases such as S1 nuclease, can also be used to remove the 5'-overhang from the nested set of 3'-deletions generated by a 3'-5'-exonuclease.

(d) Variation on the Preparation of Nested Deletions.

A number of other standard molecular biology methods for generating a nested set of deletions represent obvious variations on the original procedure. These include, but are not limited to, the use of any 3'- to 5'-exonuclease, any 5'- to 3'- exonuclease, or any endonuclease which truncates progressively from the termini of a linear DNA fragment. For example, the initial PCR amplification can be performed using the same reverse primer as above but with a forward primer which binds approximately 2 kb upstream of the start of the GST gene. This will generate a fragment in which the GST gene is flanked by >2 kb on the 5' end and only 84 bp on the 3' end. The purified PCR fragment can then be treated with Bal 31 nuclease, which progressively degrades linear duplex DNA from both the 5'- and 3'-ends. The enzyme is non-processive and the rate of degradation of the DNA depends on the time and temperature of the reaction, as well as the base composition of the DNA. Since the flanking region on the 3'-end of the GST gene in the PCR product is significantly shorter than that on the 5' end, degradation up to and beyond the stop codon will occur long before the start codon is reached from the other end. Time course experiments allow the optimum reaction conditions for removal of up to 400 bp from the 3' end of the PCR product to be determined. The resulting nested set of deletions can then be blunt-ended to remove any remaining single-stranded regions, digested with a unique restriction enzyme encoded at the 5'-end of the gene by the original vector, and directionally cloned into the tag vector. Alternatively, Lambda exonuclease can be used to generate a nested set of 5'-deletions. The preferred substrate for this enzyme is 5' phosphorylated double stranded DNA so one end of the DNA substrate can be easily protected by having a 5' hydroxyl terminus.

The single-stranded 3' overhangs of the nested set of 5'-deletions generated by a 5'-3-exonuclease can be removed by a number of different enzymes, including T4 DNA polymerase or a single-stranded DNA specific nucleases such as RNAse T or Exonuclease T or mung bean nuclease.

(e) Cloning and Analysis of the Modified Products (see FIG. 3).

The vector pMM106H (3 µg) was digested to completion with the restriction enzymes Nco I and Hpa I and the 2870 bp backbone fragment was gel purified. The vector DNA and the restricted products prepared as described above were then ligated together under standard conditions and the ligation mix was used to transform $E.$ $coli$ DH5α cells which were then recovered and plated onto LB plates containing 100 µg/ml carbenicillin.

This cloning procedure was carried out on the full set of deletions obtained in the previous step. However, only those deletions which excise the stop codon of the GST gene and end immediately after an in-frame codon should be able to give rise to in-frame fusions to the hexahistidine tag and GFP after cloning steps via this procedure; all other deletion products cloned in this manner should only lead to out-of-frame fusions to the hexahistidine tag and GFP or to unfused GST proteins, due to translational termination at the GST stop codon. This follows because ligation of the blunt end of the deletion product to the blunt end of the vector results in a genetic fusion in which the translation reading frame of the downstream vector DNA is dictated by the original reading frame of the GST coding region. If the deletion product ends in an incomplete codon, the newly appended hexahistidine-coding sequence will be out-of-frame with respect to the GST gene, whilst if the deletion product retains the GST stop codon, no translational fusion of GST to the hexahistidine tag will occur. The only hexahistidine-(and GFP-) tagged proteins which can arise from the overall process described above will therefore necessarily be GST fusions to the polyasparagine, hexahistidine tag. These will not necessarily be absolutely full-length clones, however their ability to fold correctly and retention of enzyme activity will be screened for in further steps.

Transformed colonies were visualized under UV light (365 nm) and 30 colonies (approximately 10% of the total) which fluoresced green were selected by eye for further analysis. These colonies were replica-plated and analyzed by colony Western blot under standard conditions using anti-His-tag and anti-GST antibodies. The anti-His-tag antibody only binds to colonies which express a hexahistidine-tagged protein so the Western blot gives direct information about the number of colonies expressing in-frame fusions to the hexahistidine-tag. The anti-GST antibody, on the other hand, binds close to the C-terminus of the GST protein and therefore only recognizes colonies expressing full- or nearly full-length GST proteins. The Inventors identified 19 colonies (63% of the green fluorescent colonies) containing protein which was positively recognized by both anti-His-tag and anti-GST antibodies. The DNA from 12 of these colonies was amplified, purified and sequenced. The sequencing data confirmed the presence of two perfect in-frame fusions to full length GST and 10 clones with short truncations in the GST gene, which were still in-frame with the hexahistidine tag. The frequency of isolation of full-length GST clones the Inventors obtained via this overall procedure is therefore approximately 17% (of the total number of green fluorescent colonies), while the frequency of isolation of full- or almost full-length GST clones, which are expected to retain activity, is approximately 63% (of the total number of green fluorescent colonies).

Figure 4:
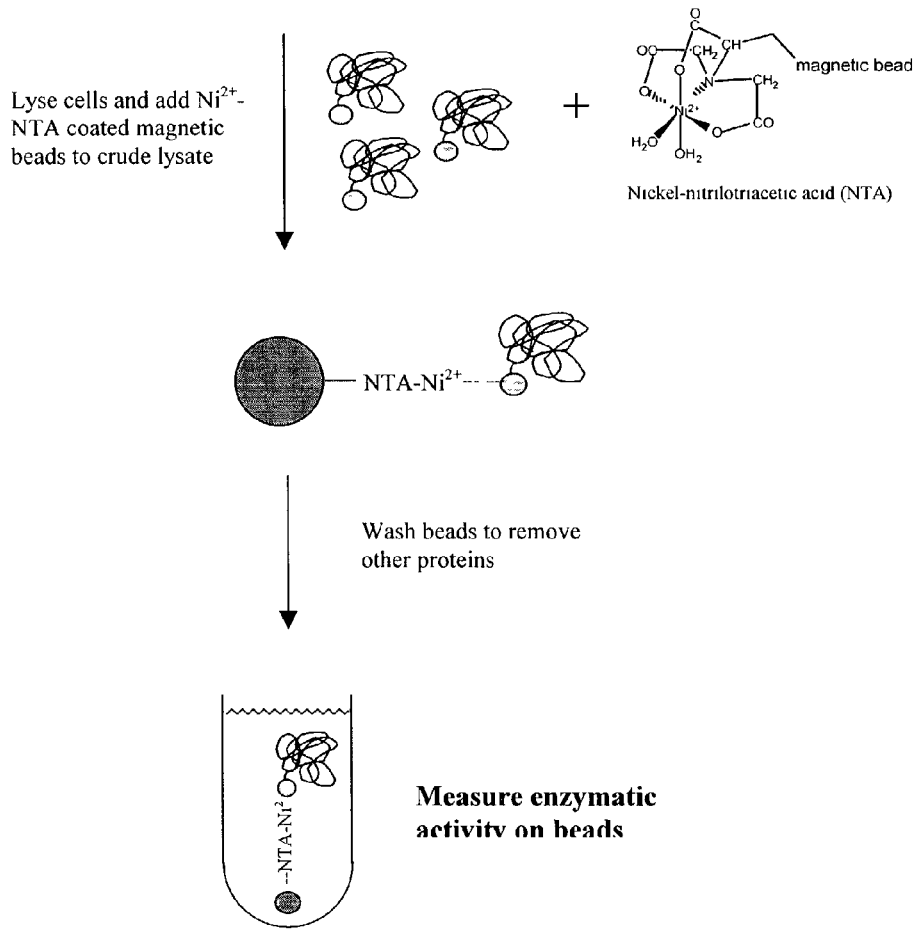
Figure 4:
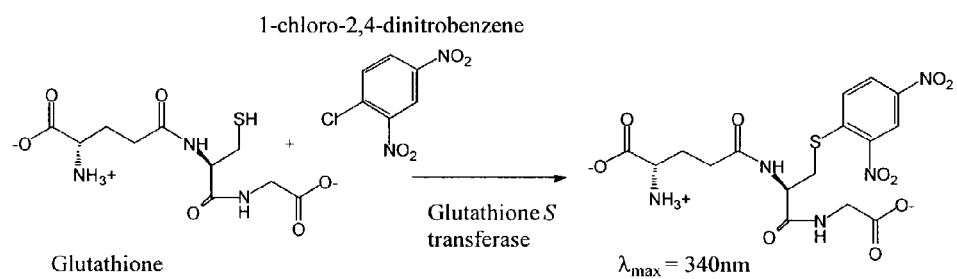

(f) Immobilization and Functional Analysis of Tagged Proteins (see FIG. 4).

$E.$ $coli$ DH5α cells were transformed with one of the full-length, hexahistidine-tagged GST plasmids created via the above methodology. A single carbenicillin-resistant colony was grown to mid-log phase in 10 ml liquid culture and then supplemented with 100 µM IPTG to induce expression of the hexahistidine-tagged GST. After growth for a further 4 hours, cells were harvested and lysed by freeze-thaw/lysozyme. SDS-PAGE of the crude lysate showed an overexpressed protein at the expected size (27 kDa), which represented roughly 20% of total soluble protein, as well as a small amount of the 54 kDa GST-hexahistidine-GFP fusion, generated through amber suppression. The crude lysate (500 µl; 100 µg) was then mixed with Nickel-NTA magnetic beads (50 µl; binding capacity 15 µg hexahistidine-tagged protein) and the beads recovered by sedimentation under a magnetic field. The supernatant was discarded and the beads were washed and then resuspended in a glutathione S transferase assay buffer containing 1 mM each of glutathione and 1-chloro-2,4-dinitrobenzene. End point assay data was collected after 30 minutes at room temperature by measuring the absorbance at 340 nm; this wavelength corresponds to the $\lambda_{max}$ of the product of the GST-catalyzed reaction.

As controls, cultures of DH5α containing either the parent vector (pMM106H) or a plasmid encoding an unrelated His-tagged protein (alanine racemase) were grown, induced, harvested, lysed and assayed in parallel. GST activity was only detected on the beads which had been mixed with the crude lysate containing the His-tagged GST, clearly demonstrating that the observed GST activity was due specifically to the immobilized His-tagged GST and moreover that the protein retained activity on specific immobilization.

After completion of the enzymatic assay, protein was eluted from the magnetic beads by addition of buffer containing 100 mM imidazole and analyzed by SDS-PAGE. This showed that the sample which gave the positive activity assay result contained a single immobilized protein of the exact size expected for glutathione S transferase (27 kDa), thus confirming that the observed activity on the beads was due to this recombinant His-tagged protein alone.

EXAMPLE 2

(a) Vector Construction.

The Inventors constructed a second vector, pMM111, which is essentially the same as pMM106H (see Example 1), except that the 676 bp Nco I/Hpa I nonsense DNA stuffer fragment is replaced with a 300 bp Nco I/Hpa I fragment derived from the *Escherichia coli* gdhA gene; the Hpa I cloning site is replaced with a Sma I site, positioned such that the downstream hexahistidine tag is out of frame with the gdhA gene by 2 nucleotides; and the ATG start codon of the GFP gene is replaced with the codon for alanine (GCG). The vector has been designed such that an insert cloned into the Sma I site must contain the first nucleotide of a codon at its 3' end to put it in frame with the hexahistidine tag and GFP. The construction of pMM111 was confirmed by sequencing.

(b) Modification Procedure to Introduce Tag.

The Inventors then carried out a procedure identical to that described in Example 1 except for the following modifications. Firstly, only α-S-dTTP was incorporated in the original PCR amplification, i.e. reaction number 3 in section (b). Secondly, the final products were cloned in to the Nco I and Sma I sites of the vector pMM111.

This procedure has several theoretical advantages over that described in Example 1. These arise principally from the statistics associated with incorporation of a single α-thio dNTP in to the original PCR products. Thus, upon exhaustive exonuclease III digestion, the nested set of 3'-recessed deletions will all now terminate with a 3'-thymidine base rather than with any of the four nucleotides. Cloning of these fragments into the Sma I site of pMM111 will only result in an in-frame fusion to the hexahistidine tag and GFP if the 3'-T is either that of the first in-frame stop codon of the GST gene or precedes, and is in the same reading frame, as the 'T' of the first in-frame stop codon (this follows because digestion with Sma I results in a gap of 2 nucleotides before the coding sequence of the tag).

Statistically, 4-fold fewer nested deletions will be created by the exonuclease hydrolysis in this modified procedure than in Example 1. However, since all three possible stop codons contain 'T' as their first base, they will all be represented in the set of deletions and will therefore constitute a four-fold higher fraction of the full set of deletions. Given the probability of any given 'T' being in the same reading frame as the first 'T' of the stop codon, 33% of all clones resulting from this modified procedure should be in-frame fusions to the His tag encoded by the vector but those deletions which affect folding (and hence function) give rise to 'white' colonies (for the reasons set out in Example 1). The Inventors have found that following this modified procedure, the fraction of precise, full length clones within the 'green' population is significantly higher than that found following the procedure in Example 1. The same argument hold of course for 'start' codons since all known start codons (ATG, GTG, TTG, ATT, CTG) contain a 'T' in the second position.

A further advantage of this modified procedure is that a polyA tail can be incorporated into the 5'-end of the forward primer used in the initial PCR amplification (e.g. Forward-A 5'-AAA AAA AAA AAA GAT CGA TCT CAT GAC GGA TAA CAA TTT CAC ACA GG-3') (SEQ ID NO:5). During amplification with a dTTP:α-S-dTTP ratio of 3:1, there is a high probability then that at least one α-S-dTTP residue will be incorporated at the end of the complementary strand, at the 5' end of the PCR product. These incorporated nucleotides will be resistant to Exonuclease III digestion and will therefore remove the requirement for enzymatic steps in specifically protecting that end of the PCR product from degradation.

EXAMPLE 3

(a) Modification of a Second Protein Using the Hexahistidine Tag.

Following the procedure as described in Example 1 for glutathione-S-transferase, the Inventors have demonstrated that the procedure is independent of the sequence of the gene being manipulated.

Thus starting with a plasmid encoding human transcription factor NF-κB p50 and following exactly the procedure described in Example 1 unless otherwise specified, the Inventors have been able to demonstrate the modification of NF-κB p50 such that the first in-frame stop codon has been excised and replaced by an in-frame fusion to DNA encoding a polyasparagine, hexahistidine tag and GFP (when the amber stop codon is suppressed). The clones that fluoresced green, when excited with far uv light (365 nm) were further characterized. Colony Western blots using an anti-His-tag antibody allowed identification of clones expressing hexahistidine-tagged protein. The soluble protein lysates of these clones were resolved by SDS-polyacrylamide gel electrophoresis and probed with anti-His tag antibody. Immunoreactive signals were observed at approx. 65 kDa $M_r$ (corresponding to translationally fused NF-κB p50 to the hexahistidine tag and GFP) and at approx. 38 kDa $M_r$ (NF-κB p50-histag). In addition there was a signal at around 27 kDa $M_r$, which is probably a degradation product corresponding to the his tagged GFP protein. The sequencing data confirmed that several clones encoded perfect in-frame fusions of full- or almost full-length NF-κB to the hexahistidine tag. In a single experiment, 190 colonies were screened for green fluorescence. A total of 38 clones (20% of the total number of clones screened) fluoresced green when excited with far uv light (365 nm). Colony western blotting using anti-His tag antibody revealed that 29 of the 38 clones expressed the hexahistidine tag. Sequencing data confirmed that 18 of these clones were full-length, or close to full length, in-frame fusions of NF-κB p50 to the hexahistidine tag; 7 of these clones were absolutely full length, His tagged NF-κB p50 genes and the remaining 11 His-tagged clones had short truncations of 4 to 1 amino acid residues. This experiment clearly demonstrates the advantage of having a reporter system indicative of expression and proper folding of the protein. Roughly 50% of the clones that fluoresced green were full length in-frame fusions to a His tag, or had minor truncations which did not cross a domain boundary, fused in-frame to a His tag.

(b) Immobilization and Functional Analysis of Hexahistidine-tagged NF-κB p50.

E. coli DH5α cells were transformed with one of the full-length, hexahistidine-tagged NF-kB plasmids created via the above methodology. A single carbenicillin-resistant colony was grown to mid-log phase in 10 ml liquid culture and then supplemented with 100 μM IPTG to induce expression of the hexahistidine-tagged NF-kB p50. After growth for a further 4 hours, cells were harvested and lysed by sonication. SDS-PAGE of the crude lysate showed an overexpressed protein at the expected size (38 kDa) which represented roughly 5% of total soluble protein.

```
κB motif
5'-CGT ATG TTG TGG GGA ATT CCC AGC GGA TAA C-3'

3'-GCA TAC AAC ACC CCT TAA GGG TCG CCT ATT G-5'
NF-KB P50 binding site
```

A duplex oligonucleotide, 'κB motif', which contains a palindromic binding site for NF-κB p50, was labeled at the 3'-bases with digoxigenin using 3-terminal transferase under standard conditions.

The protein lysates were prepared using the lysozyme/freeze-thaw method in PBS (phosphate buffered saline pH 7.5) containing 5 mM β-mercaptoethanol. 200 μl of the soluble protein lysate from each clone, was applied to the Ni-NTA coated microwell and incubated at room temperature for 45 minutes. At the end of the incubation period, the wells were washed three times with PBST (PBS containing 0.02% Triton X-100) to remove all the unbound proteins. The wells were washed three times with DNA binding buffer (10 mM Tris.HCl pH 7.4, 75 mM KCl containing 5 mM β-mercaptoethanol with a soak time of 1 minute. The 3' digoxigenin labeled κB motif (2 pmol) was added to the wells in 200 μl of the DNA binding buffer containing 1 μg of poly (dI-dC) non-specific DNA. After another 30 minutes incubation the unbound DNA was removed by washing the wells three times with 10 mM Tris.HCl pH 7.4, 25 mM KCl containing 0.02% Triton X-100. An anti-digoxigenin antibody-alkaline phosphatase conjugate was diluted to 150 mU/ml in 'antibody dilution buffer' (10 mM Tris.HCl pH7.4, 25 mM potassium chloride) supplemented with 0.2% bovine serum albumin. The diluted antibody (200 μl) was then applied to the microwells. After 30 minutes at room temperature, unbound antibody was removed by washing the microwells with 'antibody dilution buffer' (3×350 μl) supplemented with 0.02% Triton X-100. 200 μl of a buffer (100 mM Tris.HCl pH9.5, 100 mM NaCl, 50 mM $MgCl_2$) containing 250 μM p-nitrophenyl phosphate (pNPP), an alkaline phosphatase substrate, was then added to the wells and the reaction allowed to proceed overnight at room temperature, after which the yellow coloration in each well (corresponding to formation of the product, p-nitrophenol) was quantitated at 405 nm. The background rate of hydrolysis of the substrate pNPP was low so a positive assay result was therefore immediately clear from the appearance of yellow color in the wells.

As controls in this assay the Inventors omitted either the crude lysate, or the labeled oligonucleotide, or the antibody, or added a 20-fold excess of unlabelled duplex oligo or replaced the hexahistidine-tagged NF-κB p50 containing crude lysates with equivalent amounts of a crude cell lysate from DH5α cells expressing hexahistidine-tagged GST in the same vector background.

In this assay, NF-κB p50 first binds to the labeled oligonucleotide via the specific binding site. The protein-DNA complex is then immobilized in the microwells via the hexahistidine tag and all other proteins (including complexes between the labeled oligo and other DNA binding proteins present in the crude lysate) together with any unbound, labeled oligo, are then washed away. Since the antibody-conjugate recognizes the label on the oligo, not the hexahistidine-tagged protein, a positive signal in the assay can only be observed if the NF-κB p50-DNA interaction is maintained on immobilization of NF-κB p50 via the tag; if this interaction is not maintained, the oligo will be lost during the washing steps so no color change will be observed.

The Inventors found that the yellow product was only detected in the microwells which had contained the hexahistidine-tagged NF-κB p50 crude lysate and the digoxigenin-labeled oligonucleotide and to which the anti-digoxigenin antibody-alkaline phosphatase conjugate had been added. This demonstrated that the observed color change was due specifically to the immobilized NF-κB p50-oligonucleotide complex and moreover that NF-κB p50 retained activity on specific immobilization.

EXAMPLE 4

(a) Identification of One Protein from a Pool of 10 Genes.

The Inventors have applied the procedure exactly as described in Example 1 except where specified to the pool of 10 different genes listed in the table below. The Inventors have generated arrays of the resultant specifically modified proteins such that each position in the array corresponds to a single recombinant protein immobilized through the tag appended as a result of this procedure. The Inventors have then screened the array by functional assay and have successfully identified individual protein components of the pool.

TABLE 1

Size and function of the ten genes in the pool.

| Gene | Size | Source and Function |
|---|---|---|
| glutathione S transferase | 950 bp | Bacterial; detoxification |
| NF-κB p50 | 1165 bp | human; transcription factor |
| maltose binding protein | 1325 bp | bacterial; carbohydrate transport |
| alanine racemase | 1342 bp | bacterial; cell wall biosynthesis |
| nuclear factor of activated T cells (NFAT) | 1087 bp | murine; transcription factor |
| indoleglycerolphosphate synthase | 1528 bp | bacterial; amino acid biosynthesis |
| phosphoribosylanthranilate isomerase | 920 bp | bacterial; amino acid biosynthesis |
| tryptophan synthase (α-subunit) | 1122 bp | bacterial; amino acid biosynthesis |
| chymotrypsin inhibitor 2 | 389 bp | barley; serine protease inhibitor |
| β-lactamase | 1040 bp | bacterial; antibiotic resistance |

Initially, all ten genes were subcloned in to the same pTrcHisA vector backbone since amongst other things this mimics the situation encountered with a cDNA library. The primers 'STforward' and 'STreverse' described in Example 1 were designed to be universal primers for the amplification of genes encoded within a pTrcHisA vector backbone.

The primer 'STforward' was designed such that it encodes a number of restriction sites as follows:

```
5'-ATG CTG ACG TCA TGA GGC CCA TGG GGC CCG
GAT AAC AAT TTC ACA CAG G-3'
        Aat II   Bsp HI      Sfi I
```

Thus, either of the restriction enzymes Aat II or Sfi I can be used to generate 3'-overhangs for exonuclease protection purposes. For directional cloning purposes at the end of the modification procedure, in this Example the Inventors chose to use Bsp HI since although statistically it will cut more frequently within a library, it generates cohesive ends which are compatible with the Nco I cloning site in the tag vector pMM106H used here and does not cut within any of the 11 genes in the present pool. Clearly, in principle any of the primer encoded restriction sites could be used providing that the tag vector contains an equivalent cloning site downstream of the promoter; Sfi I would have significant advantages in this regard in a larger library format because it has an 8 bp recognition sequence so the frequency of random occurrence of an Sfi I site within a given gene will be much lower (1 in $6.5 \times 10^4$) than that for a 6 bp recognition sequence such as that of Bsp HI (1 in 4,096).

The tag vector pMM106H is an 'ATG' vector, i.e. the 5'-cloning site (Nco I) overlaps the ATG start codon positioned downstream of a ribosome binding site (RBS) for expression of native proteins. However, in the procedure described here the Inventors are not reliant on the cloned genes having a common restriction site at their start codons. Instead, the Inventors simply rely on the vector-encoded promoter initiating transcription to produce mRNA, with the requisite signals for translational initiation being provided by the cloned genes themselves. Thus in this Example, all the genes in the original pool have a start codon immediately preceded by an RBS, irrespective of the presence or absence of a cloning site at the ATG. Since the primer 'STforward' binds upstream of the RBS in all eleven initial clones, subsequent post-modification cloning using any of the primer encoded restriction sites will introduce the newly modified genes in to the tag vector together with their original RBS and ATG so translation initiation will be ensured. In a cDNA library format, a similar situation applies in that all full-length cDNAs will have their own 5'-untranslated regions (UTR) which contain the eukaryotic translational initiation signals. All that is required to obtain proper translational initiation then is to clone each modified cDNA together with its 5'-UTR in to a eukaryotic vector which provides transcriptional initiation signals so an equivalent universal set of PCR primers to those used in this Example could therefore be used in the modification of every member of a cDNA library in a single pot in a sequence-independent manner.

The experimental procedure was carried out as described in Example 1 with the following modifications. An equimolar pool of all ten genes was used as the template for initial PCR amplification using primers 'STforward' and 'STreverse', after which fragments were digested with Aat II to protect the 5' end. Exonuclease III and mung bean nuclease-treated fragments were generated exactly as in Example 1 and were then digested with Bsp HI, which restricts the fragments uniquely within the forward PCR primer binding site and generates a cohesive end for cloning into the vector pMM106H. The resulting fragments were gel purified and ligated in to the vector. Transformed cells were visualized under UV light (365 nm) and colonies which fluoresced green were selected by eye for analysis by Western blot. Approximately 2% of the total number of transformed colonies fluoresced green. Of these, 103 (42%) expressed proteins which are recognized by anti-His tag antibodies. These colonies were inoculated individually into 1.5 ml of liquid medium in 96-deep-well blocks and grown overnight. Cells were harvested by centrifugation and lysed by freeze-thaw/lysozyme. The individual crude lysates were then applied to individual wells of a Nickel-NTA-coated 96-well plate and unbound proteins were removed by washing, leaving a discrete His tagged recombinant protein immobilized in each well. The immobilized proteins were then assayed for either GST or NF-κB activities using the assays described in Examples 1 and 3 and wells containing positive 'hits' were identified in each case by the appearance of either green or yellow coloration respectively.

In the first assay, three proteins in the array were found to exhibit GST activity, giving a hit rate of approximately 3%. Sequencing of the corresponding plasmids revealed that all three encoded in-frame fusions between a GST gene and the hexahistidine tag and GFP gene; of these three, two were absolutely full-length GST and one was a slight truncation which clearly did not affect activity.

In the second assay, three proteins in the array showed positive 'κB-motif' DNA binding activity. Further characterization of the positive clones, showed two of the clones were in-frame fusions of the NF-κB p50 gene to the hexahistidine tag, one of which was almost full length (truncated by one amino acid) whilst the other was more severely truncated but contained the entire DNA binding domain of NF-κB p50. Interestingly, since the assay is designed for binding to the cognate DNA sequence, truncations that still have the DNA binding domain intact, folded, and functional will be positive in the assay. The third clone was found to be an in-frame fusion of the DNA binding domain of the murine transcription factor NFAT to the His tag. The 3'-digoxigenin labeled 'κB motif' used in the assay contains a specific, high affinity ($K_d$ approximately pM) binding site for NF-κB p50 but this same binding site is also specifically recognized by the DNA binding domain of NFAT with approximately nM affinity. This result therefore demonstrates that functional interrogation of arrays generated by this procedure can identify both specific interactions and also weaker interactions which are nonetheless specific and biologically relevant.

In a subsequent experiment, an array containing ca. 340 of His-tagged proteins was prepared according to the method of this Example. Analysis of the array by GST activity assay showed that 8% of all proteins in the array possessed strong GST activity. In addition, PCR analysis was carried out on a pool of the 340 encoding plasmid DNAs using gene-specific primers and this showed that each gene was represented in the His-tagged collection. These data therefore provide further confirmation that the method of this example is sequence-independent and can be applied to a collection of different genes.

In summary therefore, the Inventors have used the procedures described in these Examples to create arrays of functional proteins in a microwell format and using these arrays the Inventors have successfully identified three different proteins from a pool based on either specific protein-ligand interactions (GST activity assay) or specific protein-DNA interactions (NF-κB binding assay).

EXAMPLE 5

Creation of a cDNA Library in which Each Encoded Protein can be Solubly Expressed and has been Tagged at the C-terminus with a Common Marker in a Sequence Independent Manner The Inventors have applied a modified version of the procedure described in Example 1 to a human cardiac cDNA library containing ~5×10$^6$ discrete clones, the procedure being carried out on the entire library in a single pot. The resultant new library of DNA molecules is an expression library that contains many variants of each original cDNA, differing in the extent to which the 3'-untranslated region, the stop codon and the 3'-end of the open reading frame of each cDNA molecule has been removed and replaced with DNA encoding a common marker moiety. A subset of this new library encodes proteins that have in-frame fusions to the marker moiety. This common marker moiety then allows the expression and folding of each encoded protein within this subset to be assessed and therefore enables the identification of a further subset of the new library of DNA molecules that encodes solubly expressed (and therefore most likely correctly folded), proteins, each of which is specifically tagged at its C-terminus with the marker moiety. In addition, within this subset the marker moiety also enables the specific immobilization and purification of each expressed protein under identical conditions.

The Inventors have determined that it is an advantage when working with large libraries of this type to minimize the extent to which any bias might be introduced into the population during the modification procedures in order to ensure that every member of the starting cDNA library is likely to be represented in the resultant library of tagged cDNAs. One area in which bias can readily be introduced is during PCR amplification of the original cDNA library; by its nature, PCR amplification of a library is a competitive process when carried out with common primers in a single pot and it is likely that some members of the library will amplify more readily than others under any one set of PCR conditions. Given the exponential nature of PCR amplifications, this therefore has the potential to introduce significant bias into the amplified library. The Inventors have therefore modified the procedure described in Example 1 by removing the initial PCR amplification steps. As an alternative, the original library in this Example is amplified by propagation of bacterial cells containing the library in plasmid form. In order to minimize any biases which might result from different growth rates of bacterial cells harbouring different members of the plasmid library, the library is propagated by growth as individual colonies on solid growth media rather than as a pool in liquid culture.

Once the original library has been amplified, in plasmid form, the exonuclease steps to generate a set of nested deletions can now be carried out directly on pooled and suitably linearised plasmid DNA molecules. There are numerous methods known in the art for controlling the extent of exonuclease digestion of the library, including statistical incorporation of modified nucleotides into the DNA molecules, although this is more difficult to achieve for plasmid DNA. An alternative then is to use increasing concentrations of sodium chloride to control the activity of the nuclease and to additionally limit the amount time allowed before the nuclease activity is quenched in order to obtain a specific profile of nested deletions. Statistical analysis of the 3'-untranslated regions of known human genes has shown that the average length of human 3'-UTRs is ~520 bp, with the most common length being ~2–300 bp. This information then allows experimental conditions for the exonuclease digestion of the original cDNA library to be determined such that the set of nested deletions obtained is likely to contain variants of each original cDNA in which the 3'-UTR, stop codon and a portion of the 3'-region of the open reading frame has been removed.

Another modification in this Example compared to Example 1 is the specific choice of marker moiety used. Numerous selectable (e.g. antibiotic resistant markers) or screenable (e.g. GFP) marker moieties could be used here to assess expression and folding of the proteins encoded by the final library, whilst numerous marker moieties (e.g. hexahistidine tags) could be used for subsequent immobilization and purification of expressed proteins. In this Example the Inventors have used a GFP-biotin carboxyl carrier protein (BCCP) fusion as the marker moiety because of its general suitability for such purposes; correctly folded in-frame fusion proteins are identified in a screen for GFP activity and can then be immobilized and purified via a biotin moiety attached to BCCP.

Using this modified procedure, the Inventors have been able to create a library of >30,000 solubly expressed, folded, C-terminally tagged human cardiac proteins.

(a) Vector Construction.

1. Isolation of Biotin Carboxyl Carrier Protein (C-terminal Domain of acetyl-CoA Carboxylase) from *E. coli* K 12 Strain.

The DNA sequence encoding the entire coding region of acetyl-CoA carboxylase was amplified by PCR from genomic DNA of XL1-Blue (Stratagene) cells, using the following gene specific primers:

```
accbfor1:
5' GATGGATCCGATATTCGTAAGATTAAAAAACTGATCG 3' (with
BamHI site at the 5' end); and bccprev1:
5' GATGAGCTCAAGCTTTTACTCGATGACGACCAGCGGCTCGTC 3'
(containing Sac I and Hind III sites)
```

PCR was performed with Pwo polymerase (Roche) using 30 cycles (94° C. 5 min; 94° C. 30 sec; 64° C. 1 min; 72° C. 1 min; 30 cycles; 72° C. 5 min) under standard conditions. The amplified ORF was cloned into the Bam HI and Sac I site of the *E. coli* expression vector pQE-80 (Qiagen), in-frame with the N-terminus hexahistidine tag to form the plasmid pMSC302. The construct was confirmed by DNA sequencing. The DNA sequence corresponding to the C-terminal domain of accB known as biotin carboxyl carrier protein (bccp) was amplified by PCR using the same reverse primer as above (bccprev1) and a new forward primer:

```
bccpfor1:
5'GATCTGCAGGGCTCCGCAGCAGCGGAAATCAGTGGTCACATCG 3'
(containing Pst I site for cloning and two extra
codons for glycine and serine).
```

2. Construction of Expression Vectors.

Step 1: Deletion of the hexahistidine tag from the vector pQE-80.

The vector pQE-80 was redesigned to delete the DNA sequence for the hexahistidine tag, add additional cloning sites (Not I and Sfi I) and have three different reading frames from the start ATG (pMSC301-A, -B, and -C). This was achieved by inverse PCR using the primer sets:

```
pQErev1: 5'P CATAGTTAATTTCTCCTCTTTAATGAATTCTG 3';

together with one of
pQEfwd1: 5' GCGGCCGCCCCCATTACGGCCGGATCCGCATGCGAGCTC
                                          GGTACCCCC 3'; or pQEfwd2: 5' GGCGGCCGCGGCCATTACGGCCGGATCCGCATGCGAGCT
                                          CGGTACCCCC 3'; or pQEfwd3: 5' GCGCGGCCGCGGCCATTACGGCCGGATCCGCATGCGAGC
                                          TCGGTACCCCC 3'
``` for A, B, and C reading frames respectively. PCR was performed with Pwo polymerase (94° C. 2 min; 94° C. 30 sec; 63.5° C. 1 min; 72° C. 6 min; 25 cycles; 72° C. 10 min) under standard conditions.

Step 2: Cloning of bccp.

The bccp gene sequence was cloned into the Pst I-Hind III sites of pMSC301-A, -B, and -C vectors to generate pMSC301-A/BCCP, -B/BCCP, and -C/BCCP.

Step 3: Cloning of GFP as in-frame fusion to bccp.

The DNA sequence encoding GFPuv (Clontech) beginning from codon 2, was amplified by PCR using the primer set:

```
pQEGFPfor1:
5' GGGCCGGTGGCAGCGCGAGTAAAGGAGAAGAACTTTTCACTGG 3'
(with Sma I half site and a linker region); and pQEGFPrev1:
5' GATCTGCAGGGTACCGGATCCTTTGTAGAGCTCATCCATGCC 3'
(with Pst I, Kpn I and Bam HI sites)
```

The PCR amplified product was cloned into the Sma I-Pst I sites of pMSC301-A/BCCP, -B/BCCP and -C/BCCP, in-frame to the sequence encoding the N-terminus of BCCP (GFP-BCCP) to generate the vectors pMSC303-A, -B, and -C.

Step 4: Replacing the 5' cloning sites Not I and Sfi I with Dra III.

The Not I and Sfi I cloning sites of the vectors pMSC303-A, -B and -C were replaced with the Sfi I overhang compatible restriction site Dra III, to generate the vectors pIFM101A, B, and C. This was achieved by inverse PCR using the primers:

```
    DrafwdA:
    5' CACTTAGTGGGATCCGCATGCGAGCTCGGTACCCC 3'; and

DrafwdB:
    5' G + DrafwdA; DrafwdC: GA + DrafwdA.
```

The reverse primer used was pQErev1 as described earlier. The PCR was performed with Pwo polymerase (94° C. 2 min; 94° C. 30 sec; 63.5° C. 1 min; 72° C. 6 min; 25 cycles; 72° C. 10 min) under standard conditions.

Step 5: Cloning of a stuffer fragment containing the stop codon TAA in three reading frames.

A stuffer fragment harbouring the stop codon 'TAA' in three reading frames was generated by annealing the two complementary oligos:

```
StufferF:
5' CGTAAATAACTAAATGATATCGAGCTCGGTACC 3'; and

StufferR:
5' CCGGGGTACCGAGCTCGATATCATTTAGTTATTTACGCATG 3'.
```

Figure 5:
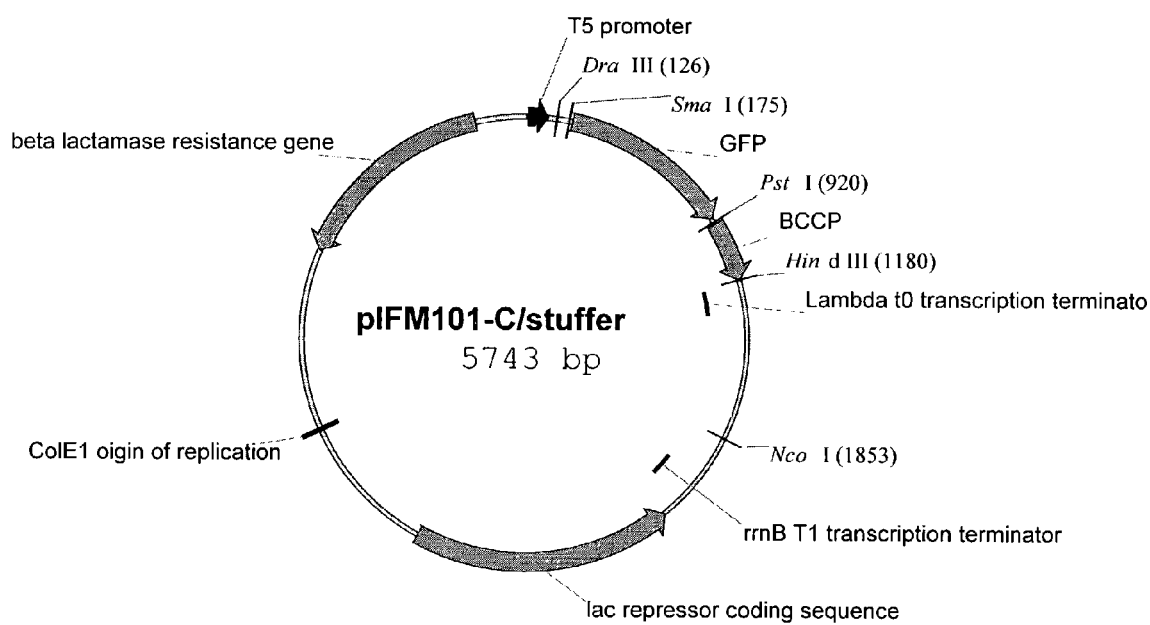
Figure 6:
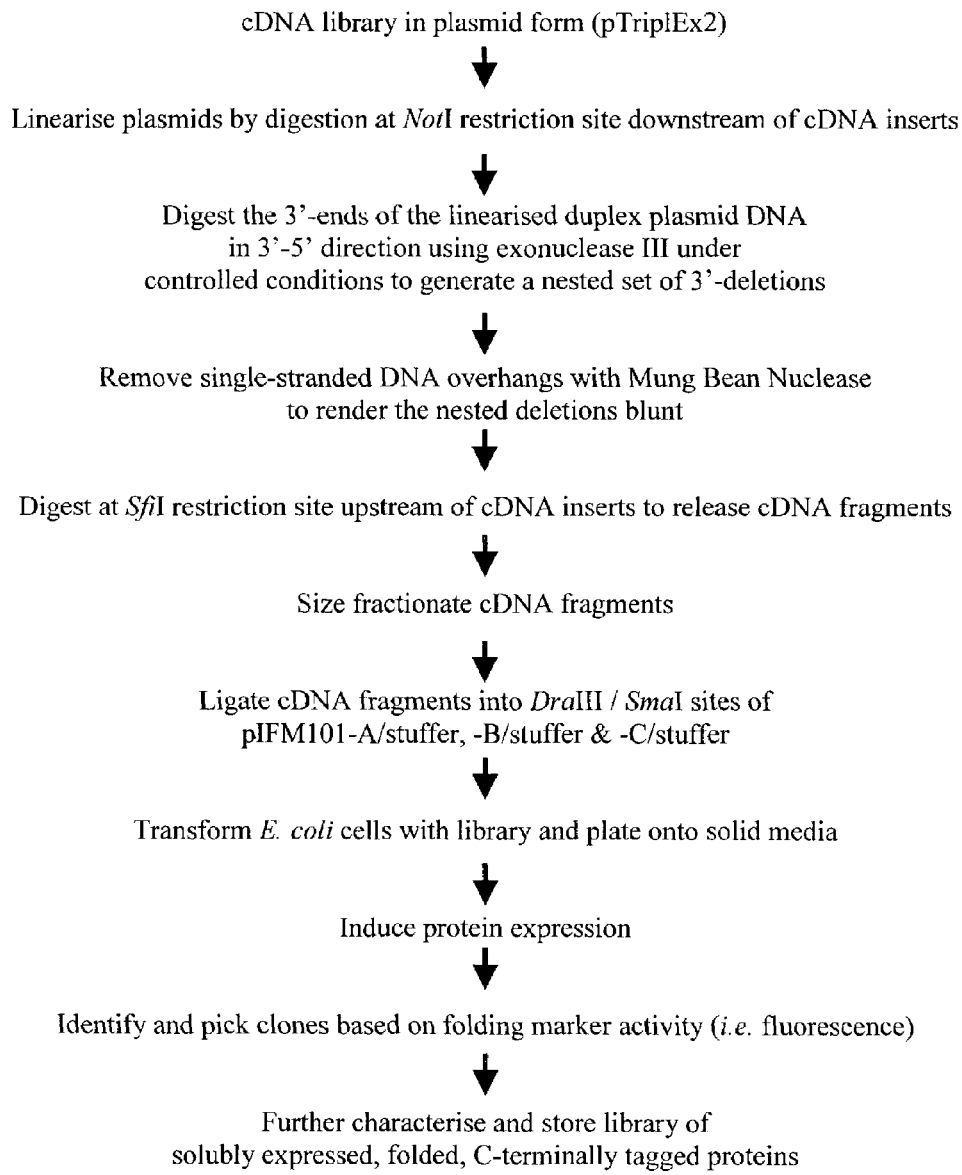

The annealed duplex DNA with Sph I and Xma I overhangs was directionally cloned into Sph I and Xma I sites of pIFM101-A, -B, and -C to form pIFM101-A/stuffer, -B/stuffer and -C/stuffer (FIG. 5).

The correct DNA sequence of all the constructs used in the study was confirmed by sequencing.

(b) Generation of a Modified Human Cardiac Expression Library.

Source of Full-Length Human Heart cDNAs:

A human heart large-insert cDNA library was obtained from Clontech. The cDNAs were cloned into the Sfi I A and Sfi I B sites of the lambda vector (λTriplEx2). The library was converted into a plasmid format (pTriplEx2) by site-specific recombination mediated by cre-recombinase at the loxP sites, according to the manufacturer's instructions. Approximately $5 \times 10^6$ cfu were pooled to prepare plasmid DNA which was used as the source of a set of human heart cDNAs.

Controlled deletion at 3' ends of cDNAs using exonuclease III:

The pTriplEx2 plasmid DNA (80 µg) was restricted with Not I (unique site present 33 bp 3' to Sfi I B) to generate recessed 3' hydroxyl ends downstream of the 3' UTR of the cloned cDNAs. The linearised plasmid DNA was purified using a QIAquick PCR cleanup kit (Qiagen) and then treated with exonuclease III (NEB). The digestion was performed under controlled conditions so as to generate a set of nested deletions (approximately 300 to 500 bp) of the sense strand from the 3' end of the cDNAs. The reactions were performed in a standard exonuclease III buffer plus/minus additional NaCl (50 mM) to control the rate of digestion such that the majority of the nested deletions obtained ranged from 100 bp to 400 bp (plus salt) or 100 bp to 600 bp (minus salt), roughly matching the average length of human 3'-UTRs.

The linear plasmid DNA (2.5 µg) was incubated with 75 units of exonuclease III (30 u/µg DNA) in 50 µl of standard reaction buffer plus/minus additional NaCl (50 mM). Reactions were set up on ice then incubated at 25° C. for 2 mins and stopped by adding PB buffer from the QIAquick PCR clean up kit. The 0 and 50 mM NaCl samples were pooled and the DNA purified using a QIAquick column.

(c) Removal of Single-Stranded DNA Overhangs and Cloning into the Expression Vectors.

Mung Bean Nuclease (MBN; New England Biolabs) was used to remove ssDNA from the antisense strand. The reaction was performed in standard MBN buffer using 2 units of MBN per microgram of DNA at 30° C. for 30 mins. At the end of the incubation period, EDTA was added to a final concentration of 5 mM to stop the reaction. The MBN-treated DNA was concentrated by ethanol precipitation, restricted with Sfi I, and resolved on a 0.8% agarose gel. DNA was excised from the gel in fractions according to size and purified using a QIAquick gel purification kit (Qiagen):

1. 0.5 to 1 kb
2. 1 to 1.6 kb
3. 1.6 to 3 kb
4. 3 to 3.6 kb (this fraction contains original vector backbone region as well as cDNA inserts)
5. 3.6 to 4 kb The DNA eluted from fraction 4, which would additionally contain the original vector backbone region as well as cDNA inserts of this size range, was restricted with BssH II (unique site present upstream of Sfi I A) to make one end of the original vector backbone fragments non-ligatable. Each pool of size fractionated DNA was cloned into the Dra III-Sma I sites of pIFM101-A/stuffer, -B/stuffer, and -C/stuffer and used to transform ultracompetent XL 10-Gold cells (Stratagene) following standard procedures.

(d) Screening Transformants for GFP Activity.

The transformants were plated onto nitrocellulose or nylon membranes (Amersham) placed on LB agar containing carbenicillin (100 μg/ml). Following overnight incubation at 37° C., membranes were transferred onto LB agar containing carbenicillin (100 μg/ml), IPTG (400 μM) and biotin (50 μM) and incubated at 30° C. for 4 hrs. Plates were stored overnight at 4° C. before visualizing the green fluorescence of in-frame fusion proteins to GFP by illumination of clones at 365 nm on a UV-transilluminator. Positive (i.e. fluorescent) clones were identified and picked robotically or manually, grown overnight in 96 or 384 well plates in freezing medium and then stored at −80° C.

In total, the library comprised approximately 7.5×10$^5$ cfu, of which in excess of 30,000 clones were positive (Table 1). The percentage of green clones varied with the size range of the insert. As expected, the smaller insert fractions yielded a higher percentage of green clones than the larger inserts, but even the largest insert size range (i.e. 3.6 to 4 kb) gave rise to a significant number of positive clones.

TABLE 2

Efficiency of cloning procedure.

| Insert size range cloned | Fraction of overall clones obtained that express a soluble GFP-BCCP fusion protein (%) | Total number of fluorescent colonies obtained in each insert size range |
|---|---|---|
| 0.5 to 1 kb | 7 | 16,800 |
| 1 to 1.6 kb | 5 | 9,840 |
| 1.6 to 3 kb | 3 | 5,760 |
| 3.6 to 4 kb | 0.1 | 240 |
| | | TOTAL = 32,640 |

(e) PCR screen of modified ORFs.

A colony PCR screen on a representative sample of positive clones (96) was performed using vector specific forward and reverse primers flanking the cloned insert. The forward primer MD12 (5' TATCACGAGG CCCTTTCGTCTTCA 3') (SEQ ID NO: 19) binds approximately 100 bp upstream of the start 'ATG' and the reverse primer GFPseq-rev (5' TTCACCCTCTCCACTGACAG 3') (SEQ ID NO:2) binds approximately 100 bp downstream of the start of GFP. PCR was performed using Taq polymerase (Roche) under standard conditions. The cycling conditions were 94° C. 10 mins; 94° C. 30 sec; 52° C. 1 min; 72° C. 5 mins; 35 cycles; 72° C. 10 mins. PCR products were resolved on a 0.8% agarose gel. Inserts ranged in size from 0.6–3.3 kb with an average insert size of 1.2 kb. Less than 8% of clones contained either very small (<200 bp) or no inserts.

The average insert size observed here compares very favorably with the average gene size estimated from the first draft of the human genome to be ~1.4 kb, suggesting that the modification procedure described here produces substantially full length, tagged proteins as expected.

(f) Western Blot Analysis of the Expressed Fusion Proteins.

A representative set of clones (48) were grown in liquid culture to mid-log phase and then induced with 400 μM IPTG, in the presence of 50 μM biotin. Cells were harvested 3 hours later, extensively washed and then lysed by incubation at 75° C. in SDS loading buffer. The presence of biotinylated recombinant fusion proteins was demonstrated by binding of streptavidin-horseradish peroxidase (HRP) conjugate (Amersham) on western blots using standard procedures. Fusion proteins in excess of 100 kDa were detected from several clones, consistent with the cDNA insert size in these clones. Approximately 80% of clones produced a fusion protein detectable by binding to a streptavidin-HRP conjugate, indicating that they were both expressed and biotinylated. Recombinant proteins were detectable in many cases by Coomassie-staining of proteins following SDS-PAGE of the crude lysates Approximately 20% of the clones appeared to have a small peptide linked to GFP-BCCP, although the insert size predicted a larger protein. This could be due to initiation of translation from pseudo RBS (ribosome binding sites) close to the GFP sequence. Alternatively, it could indicate that the expressed fusion protein is unstable and undergoes rapid degradation prior to analysis.

(g) Sequence Analysis of a Subset of Clones.

A subset of clones expressing correctly folded and biotinylated fusion proteins were analyzed by DNA sequencing. The identity of the ORFs was assigned following a BLAST search and are listed below (Table 3). There was found to be less than 10% redundancy.

TABLE 3

Identity of tagged genes determined by DNA sequencing.

| Open Reading Frame | Accession No. |
|---|---|
| *Homo sapiens* ribosomal protein S8 (RPS8) | NM_001012 |
| *Homo sapiens* golgi autoantigen (with transmembrane signal), 1 (GOLGB1) | NM_004487 |
| *Homo sapiens* heat shock 90 kD protein 1, alpha (HSPCA) | NM_005348 |
| *Homo sapiens* amyloid beta (A4) precursor protein (protease nexin-II, Alzheimer disease) (APP) | NM_000484 |
| *Homo sapiens* eukaryotic translation elongation factor 1 delta (guanine nucleotide exchange protein) | BC012819 |
| *Homo sapiens* similar to BAG-FAMILY MOLECULAR CHAPERONE REGULATOR-2 | XM_038325 |
| *Homo sapiens* NADH dehydrogenase (ubiquinone) Fe-S protein 4 | NM_002495 |
| *Homo sapiens* hydroxyacyl-Coenzyme A dehydrogenase/3-ketoacyl-Coenzyme A thiolase/enoyl-Coenzyme A hydratase (trifunctional protein), beta subunit (HADHB) | NM_000183 |
| N-ter part *Homo sapiens* similar to signal recognition particle | XM_057253 |
| *Homo sapiens* ribosomal protein, large, P0 (RPLP0), transcript variant 1 | NM_001002 |
| Human heart mRNA for heat shock protein 90 | D87666 |
| Human DNA sequence from clone RP3-388E23 on chromosome 6q22.33–24.1 | |
| *Homo sapiens* PDZ domain protein (Drosophila inaD-like) (INADL), | NM_005799 |
| *Homo sapiens* hypothetical gene supported by S63912 | XM_011901 |
| *Homo sapiens* zinc metalloproteinase, STE24 (yeast, homolog) (ZMPSTE24), | XM_029836 |
| *Homo sapiens* similar to nebulin-related anchoring protein (*H. sapiens*) | XM_058387 |
| *Homo sapiens* similar to titin (*H. sapiens*) (LOC129826) | XM_038278 |
| WDC146 | AB044749 |
| *Homo sapiens* AHNAK nucleoprotein (desmoyokin) (AHNAK) | XM_043308 |
| *Homo sapiens* HDCMA18P protein (HDCMA18P) | BC006981 |
| *Homo sapiens* ribosomal protein L3 (RPL3) | XM_039345 |

TABLE 3-continued

Identity of tagged genes determined by DNA sequencing.

| Open Reading Frame | Accession No. |
|---|---|
| *Homo sapiens* pleiotropic regulator 1 (PRL1, Arabidopsis homolog) (PLRG1) | NM_002669 |
| *Homo sapiens* Huntington interacting protein K (HYPK) | NM_016400 |
| *Homo sapiens* calpastatin | AF327443 |
| *Homo sapiens* Ste20-related ser/thre kinase (SLK) | NM_014720 |
| *Homo sapiens* ribosomal protein L4 (RPL4) | NM_000968 |
| *Homo sapiens* isocitrate dehydrogenase 1 (NADP+), soluble (IDH1). | XM_028869 |
| *Homo sapiens* dihydrolipoamide dehydrogenase mRNA | XM_027212 |

In each case, the ORF was found to be fused in-frame to the GFP-BCCP tag, as shown by the examples below:

a new library is created in which each individual member expresses a soluble, folded, C-terminally tagged protein. Clearly the expression host could be eukaryotic (e.g. *Pichia pastoris, Saccharomyces cereviseae*, insect cells, CHO cells, etc.) rather than prokaryotic (e.g. *E. coli*) and it is expected that use of such eukaryotic expression hosts will increase the number of different tagged proteins that can be expressed from libraries created using these methods.

From the data, it appears that there is no apparent introduction of redundancy resulting from the methods described in this Example and this method therefore represents an efficient, sequence independent means of generating a library of solubly expressed, tagged proteins derived from any starting cDNA library. The proteins of this final library are suitable for many applications including, but not limited to, creation of arrays of folded, functional, proteins specifically immobilized through the marker moiety in each case.

```
              (1265) 1265  1270      1280      1290      1300      1310      1320      1330      1340      1351
GFP              (1) ---------------------------------------------GCGAGTAAAGGAGAAGAACTTTTCACTGGAGTTG
from p
101A
BAG            (817) AGAAAATTAAGAGAAGATTAAAGACTCTGCTTAGAAATAGGGCCGGTGGCAGCGCGAGTAAAGGAGAAGAACTTTTCACTGGAGTTG
Chaper-
one reg-
ular-2
HADHB         (1015) GTGCATCTGCAATGTTAATCATGGCGGAGGAAAAGGCTCGGGCCGGTGGCAGCGCGAGTAAAGGAGAAGAACTTTTCACTGGAGTTG
RPLP0          (851) AGGTTGAAGCCAAGGAAGAGTCGGAGGAGTCGGACGAGGGGGCCGGTGGCAGCGCGAGTAAAGGAGAAGAACTTTTCACTGGAGTTG
RPL3          (1244) TGGAGGAGAAGAAAGCANTCATGGGACCACTGAAGAAAGGGCCGGTGGCAGCGCGAGTAAAGGAGAAGAACTTTTCACTGGAGTTG
PLRG1          (996) AAAGTCGATTACTAACAGCTGAAGCTGATAAAACCATTAGGGCCGGTGGCAGCGCGAGTAAAGGAGAAGAACTTTTCACTGGAGTTG
HYPK           (973) CTCGAGCAGCAGCAGAACGCAGTTTGCGGGAACACATGGGGCCGGTGGCAGCGCGAGTAAAGGAGAAGAACTTTTCACTGGAGTTG
Calpas-       (1060) AGGATAAGTGCAAGAAGGCTNCTTCCAGCTCCAAAGCACGGGCCGGTGGCAGCGCGAGTAAAGGAGAAGAACTTTTCACTGGAGTTG
tatin
RPL4           (932) CTGAAAAGAAGCCTGCANAAAAGAAACCTACTACAGAGGGGGCCGGTGGCAGCGCGAGTAAAGGAGAAGAACTTTTCACTGGAGTTG
IDH1           (973) CAGAGGCTGCCCACGGGACTGTAACCCGTCACTACCGCAGGGCCGGTGGCAGCGCGAGTAAAGGAGAAGAACTTTTCACTGGAGTTG
dihydro-     (1037) TTCTTGGACCAGGTGCTGGAGAAATGGTAAATGAAGCTGGGGCCGGTGGCAGCGCGAGTAAAGGAGAAGAACTTTTCACTGGAGTTG
lipoa-
mide de-
hydro-
genase
Consen-      (1265) G          G A             AA        GGGCCGGTGGCAGGCGCGAGTAAAGGAGAAGAACTTTTCACTGGAGTTG
sus (389) 389       400       410       420       430       440         457
GFP              (1) ----------------------------------------------ASKGEELFTGVVPILVEL
from p1
FM101A
BAG            (235) LMSYLSACSSEVPHGPVDQKFQSIVIGCALEDQKKIKRRLKTLLRNRAGGSASKGEELFTGVVPILVEL
Chaper-
one reg-
ulator-2
HADHB          (299) IRPSSLEQMAKLPAFIKPYGTVTAANSSFLTDGASAMLIMAEEKARAGGSASKGEELFTGVVPILVEL
RPLP0          (242) KVKAFLADPSAFVAAAPVAAATTAAPAAAAAPAKVEAKEESEESDEGAGGSASKGEELFTGVVPILVEL
RPL3           (375) KSLLVQTKRRALEKIDLKFIDTTSKFGHGRFQTMEEEKKAXMGPLKKGAGGSASKGEELFTGVVPILVEL
PLRG1          (294) WRTGYNFQRVHAAVQPGSLDSESGIFACAFDQSESRLLTAEADKTIRAGGSAKGEELFTGVVPILVEL
HYPK           (286) SREQKAKQEREKELAKVTIKKEDLELIMTEMEISRAAAERSLREHMGAGGSASKGEELFTGVVPILVEL
Calpas-        (312) DSKKPADDQDPIDALSGDLDSCPSTTETSQNTAKDKCKKAXSSSKARAGGSASKGEELFTGVVPILVEL
tatin
RPL4           (275) PVVGKKGKKAAVGVKKQKKPLVGKKAAATKKPAPEKKPAXKKPTTEGAGGSASKGEELFTGVVPILVEL
IDH1           (286) YDGDVQSDSVAQGYGSLGMMTSVLVCPDGKTVEAEAAHGTVTRHYRRAGGSASKGEELFTGVVPILVEL
dihydro-      (305) PFAANSRAKTNADTDGMVKILGQKSTDRVLGAHILGPGAGEMVNEAGAGGSASKGEELFTGVVPILVEL
lipoa-
mide
dehydro-
genase
Consen-       (389)                                                AGGSASKGEELFTGVVPILVEL
sus
```

This Example therefore demonstrates that a whole cDNA library can be modified by the methods described such that When expressed in eukaryotic host cells, particularly mammalian cells, the tagged proteins produced by these methods can also be used in pull-down assays to identify interacting partner; such pull-downs can clearly be carried out on a one-by-one basis but could also be highly multiplexed, with the pull-down being in an array format.

EXAMPLE 6

A direct Method for Creating a cDNA Library Encoding Solubly Expressed Proteins which are Each Tagged at the C-Terminus with a Common Marker.

This Example describes an extension of the procedure described in Example 5 to allow the direct modification of cDNA molecules which have been synthesized from mRNA but have previously not been cloned. As in the previous Examples, the modification of the cDNA molecules is such that the encoded proteins are C-terminally tagged with a common marker moiety.

Every stage of the process whereby cDNA is generated from mRNA is subject to inefficiencies and has the potential to introduce bias into the resultant library. Thus, for example, RNA is subject to both enzymatic degradation by RNases and degradation by conditions such as high temperature, pH or cation concentration; different mRNAs have distinct half-lives and will degrade at different rates, thereby altering their relative concentrations. In order to prepare good quality, full length cDNA, it is therefore vital to purify RNA as quickly as possible from the source sample and stabilize it through the addition of protection agents such as RNase inhibitors or storage at low temperatures.

Similarly, the production of cDNA from mRNA can also introduce bias not present in the original sample. For example, secondary structure in the RNA can cause the reverse transcriptase (RT) to stall, producing a truncated first strand product. RT does not have proofreading activity so some misincorporation of nucleotides can also occur but other than using a higher-fidelity reverse transcriptase, these steps are obligate in cDNA synthesis.

Following synthesis of the second strand of cDNA with a DNA polymerase, the cDNA is then usually subjected to several further manipulations before cloning into an appropriate vector. These can include some or all of the following steps:

Phenol extraction and ethanol precipitation;
Polishing of ends;
Methylation;
Addition of linkers;
Digestion of cDNA for cloning;
Ligation;
Transformation;

all of which have the potential to introduce bias into the distribution of cDNA molecules in the resultant library because the cloning of some cDNA molecules may be less favored than others. There are a number of reasons why this might be the case. For example, smaller fragments may compete more effectively for vector during ligation; this could be attributable to a higher relative concentration of smaller cDNAs, particularly if there was significant stalling of the RT during cDNA synthesis or purification favored smaller fragments. Similarly, following transformation, vector molecules to which large inserts have ligated may have a growth disadvantage; it is known there are limitations to the size of plasmid which may be stably propagated in *E. Coli* and this potentially imposes limits on the size of insert which can be stably cloned. One common way of reduce such insert-size constraints during cloning is to use lambda phage vectors rather than plasmid vectors since lambda has the ability to stably clone relatively large inserts.

Finally, following generation of the library, there is typically a requirement to amplify the library at least once before use. This is usually achieved by transforming bacterial cells with the library, after which the library is propagated by growth of the resultant culture. This process again has the potential to introduce bias into the cDNA library being generated because some inserts will encode a protein that is detrimental to the host cell; in these cases, if the promoter upstream of the cloned insert is 'leaky', i.e. allows a small amount of transcription of the insert in the absence of inducing conditions, such clones will be selected against during any propagation of the library.

It is clear that a process which dispenses with the requirement to manipulate, clone and propagate the second strand cDNA population would have the potential to significantly reduce the bias that is inherent in the overall cDNA cloning process. By applying the methods of the present invention directly to second strand cDNA molecules, it is possible to reduce this bias, whilst by performing the process on a solid substrate such as sepharose beads, it is possible to maximize the recovery of products from relatively small amounts of starting cDNA.

In brief then, first strand cDNA is synthesized using an oligodT primer which also incorporates a site for a restriction enzyme that is a rare cutter (NotI) and that leaves a 5' overhang on restricted double-strand DNA. The first strand cDNA is synthesized by methods known in the art, such as the SMART™ method, which permits the addition of a known sequence to the 3' end of the first strand cDNA. Following alkaline hydrolysis of the original mRNA and removal of any short DNA primers, the second strand cDNA is then synthesized using a primer complementary to this sequence and which contains a site for a second rare cutter such as SfiI. This second strand primer is optionally biotinylated such that it can bind to streptavidin attached to a solid substrate. The primer anneals in such a manner that it forms a duplex with its complementary sequence on the first strand and forms a 3' overhang, resistant to exonuclease III. Alternatively, other methods of protecting against nuclease digestion which are known in the art can be used. Following second strand synthesis, streptavidin-coated beads are added to the reaction mix and the cDNA is captured. This now serves as a substrate for the modified procedure described in Example 5. Thus, following digestion with NotI to reveal the 5' overhang close to the oligodT sequence, exonuclease III is used to digest the top strand of the cDNA under conditions controlled to yield the desired deletion profile. The bottom, single-stranded DNA is then removed by treatment with mung bean nuclease and the ends are made flush by treatment with T4 DNA polymerase. The modified cDNA is then released from the beads by digestion with SfiI and cloned into a vector such as pIFM101-A, -B, -C, as described in Example 5, such that fusion in-frame with a C-terminal marker moiety can be achieved.

What is claimed is:

1. A method for producing one or more proteins in which one or more domains are full length and correctly folded and wherein each protein is tagged at either the N- or C-terminus with one or more marker moieties, said method comprising:
   (a) providing one or more DNA molecules having an open reading frame encoding said proteins together with 5' and/or 3' untranslated regions;
   (b) amplifying said DNA molecules under conditions that incorporate α-S-dNTPs as well as dNTPs into the daughter DNA molecules;
   (c) specifically protecting the 5' or 3' end of said daughter DNA molecules from nuclease digestion;
   (d) treating said DNA molecules first with a 3' to 5'-nuclease to generate a set of nested deletions followed by treating with a single-strand nuclease under conditions that allow removal of said 5' or 3' untranslated regions including a start codon or a stop codon of said open reading frame;
   (e) cloning the fragments generated in step (d) into an expression vector containing a coding sequence for one or more 5' or 3' marker moieties; and
   (f) expressing said encoded proteins in which one or more domains are full length and correctly folded.

2. A method as claimed in claim 1, wherein said amplification of said DNA molecule incorporates a single type of α-S-dNTP.

3. A method as claimed in claim 2, wherein the single α-S-dNTP is either α-S-dTTP or α-S-dATP.

4. A method as claimed in claim 1, wherein said nuclease is exonuclease III.

5. A method as claimed in claim 1, wherein said single-strand nuclease is mung bean nuclease or T4 DNA polymerase.

6. A method as claimed in claim 1, wherein the marker moiety allows confirmation of expression of said open reading frame.

7. A method as claimed in claim 1, wherein the marker moiety allows confirmation of folding of said open reading frame.

8. A method as claimed in claim 1, wherein the marker moiety encodes the green fluorescent protein.

9. A method as claimed in claim 1, wherein the marker moiety is a peptide sequence, a complete protein or protein domain.

10. A method as claimed in claim 9, wherein the peptide sequence is a hexa-histidine tag.

11. A method as claimed in claim 9, wherein the protein domain is the maltose binding protein domain.

12. A method as claimed in claim 10, wherein the tag allows for purification of the individual encoded proteins.

13. A method as claimed in claim 1, wherein the tag is inserted such that the start or stop codon for each of the proteins is replaced.

14. A method as claimed in claim 1, wherein the tag is inserted in-frame in a region close to the terminus of each of the encoded proteins such that the encoded proteins fold correctly and retain function.

15. A method as claimed in claim 1, wherein the tag is inserted in-frame within the open reading frame of the encoded proteins such that the encoded proteins fold correctly and retain function.

16. A method as claimed in claim 1, wherein amplification of said DNA molecule in step (a) is by a non-proof-reading polymerase.

17. A method as claimed in claim 16, wherein said non-proof-reading polymerase is a Taq polymerase or the Klenow fragment of DNA polymerase I.

18. A method as claimed in claim 1, wherein the ratio of said α-SdNTPs to dNTPs is between 1:1 and 1:3.

19. A method as claimed in claim 1, wherein said to 5'-nuclease is unable to hydrolyze α-S-phosphodiester linkages.

20. A method as claimed in claim 1, wherein said DNA molecule is a cDNA produced by reverse transcription from a mRNA sequence.

21. A method as claimed in claim 1, wherein said method is carried out on multiple different DNA molecules in parallel.

22. A method as claimed in claim 1, wherein said method is carried out on a population of DNA molecules in a single pot.

* * * * *

SEQUENCE LISTING

<160> NUMBER OF SEQ ID NOS: 46

<210> SEQ ID NO 1
<211> LENGTH: 41
<212> TYPE: DNA
<213> ORGANISM: Artificial
<220> FEATURE:
<223> OTHER INFORMATION: Primer

<400> SEQUENCE: 1
atgctgcaga cgtcaacagt atccatggcc cctatactag g            41

<210> SEQ ID NO 2
<211> LENGTH: 37
<212> TYPE: DNA
<213> ORGANISM: Artificial
<220> FEATURE:
<223> OTHER INFORMATION: Primer

<400> SEQUENCE: 2
gcgaggaagc ttgtcaatca gtcacgatga attcccg                 37

<210> SEQ ID NO 3
<211> LENGTH: 49
<212> TYPE: DNA
<213> ORGANISM: Artificial
<220> FEATURE:
<223> OTHER INFORMATION: Primer

<400> SEQUENCE: 3
atgctgacgt catgaggccc atggggcccg gataacaatt tcacacagg    49

<210> SEQ ID NO 4
<211> LENGTH: 34
<212> TYPE: DNA
<213> ORGANISM: Artificial
<220> FEATURE:
<223> OTHER INFORMATION: Primer

<400> SEQUENCE: 4
gcggatcctt gcggccgcca ggcaaattct gttt                    34

<210> SEQ ID NO 5
<211> LENGTH: 47
<212> TYPE: DNA
<213> ORGANISM: Artificial
<220> FEATURE:
<223> OTHER INFORMATION: Primer

<400> SEQUENCE: 5
aaaaaaaaaa aagatcgatc tcatgacgga taacaatttc acacagg      47

<210> SEQ ID NO 6
<211> LENGTH: 30
<212> TYPE: DNA
<213> ORGANISM: Artificial
<220> FEATURE:
<223> OTHER INFORMATION: Primer

<400> SEQUENCE: 6
cgtatgttgt ggggaattcc cagcggataa                         30

<210> SEQ ID NO 7
<211> LENGTH: 37

```
<212> TYPE: DNA
<213> ORGANISM: Artificial
<220> FEATURE:
<223> OTHER INFORMATION: Primer

<400> SEQUENCE: 7
gatggatccg atattcgtaa gattaaaaaa ctgatcg                    37

<210> SEQ ID NO 8
<211> LENGTH: 42
<212> TYPE: DNA
<213> ORGANISM: Artificial
<220> FEATURE:
<223> OTHER INFORMATION: Primer

<400> SEQUENCE: 8
gatgagctca agcttttact cgatgacgac cagcggctcg tc              42

<210> SEQ ID NO 9
<211> LENGTH: 43
<212> TYPE: DNA
<213> ORGANISM: Artificial
<220> FEATURE:
<223> OTHER INFORMATION: Primer

<400> SEQUENCE: 9
gatctgcagg gctccgcagc agcggaaatc agtggtcaca tcg             43

<210> SEQ ID NO 10
<211> LENGTH: 32
<212> TYPE: DNA
<213> ORGANISM: Artificial
<220> FEATURE:
<223> OTHER INFORMATION: Primer

<400> SEQUENCE: 10
catagttaat ttctcctctt taatgaattc tg                         32

<210> SEQ ID NO 11
<211> LENGTH: 48
<212> TYPE: DNA
<213> ORGANISM: Artificial
<220> FEATURE:
<223> OTHER INFORMATION: Primer

<400> SEQUENCE: 11
gcggccgccc ccattacggc cggatccgca tgcgagctcg gtaccccc        48

<210> SEQ ID NO 12
<211> LENGTH: 49
<212> TYPE: DNA
<213> ORGANISM: Artificial
<220> FEATURE:
<223> OTHER INFORMATION: Primer

<400> SEQUENCE: 12
ggcggccgcg gccattacgg ccggatccgc atgcgagctc ggtacccccc      49

<210> SEQ ID NO 13
<211> LENGTH: 50
<212> TYPE: DNA
<213> ORGANISM: Artificial
<220> FEATURE:
<223> OTHER INFORMATION: Primer

<400> SEQUENCE: 13
```

-continued gcgcggccgc ggccattacg gccggatccg catgcgagct cggtaccccc    50

<210> SEQ ID NO 14
<211> LENGTH: 43
<212> TYPE: DNA
<213> ORGANISM: Artificial
<220> FEATURE:
<223> OTHER INFORMATION: Primer

<400> SEQUENCE: 14
gggccggtgg cagcgcgagt aaaggagaag aacttttcac tgg    43

<210> SEQ ID NO 15
<211> LENGTH: 42
<212> TYPE: DNA
<213> ORGANISM: Artificial
<220> FEATURE:
<223> OTHER INFORMATION: Primer

<400> SEQUENCE: 15
gatctgcagg gtaccggatc ctttgtagag ctcatccatg cc    42

<210> SEQ ID NO 16
<211> LENGTH: 35
<212> TYPE: DNA
<213> ORGANISM: Artificial
<220> FEATURE:
<223> OTHER INFORMATION: Primer

<400> SEQUENCE: 16
cacttagtgg gatccgcatg cgagctcggt acccc    35

<210> SEQ ID NO 17
<211> LENGTH: 33
<212> TYPE: DNA
<213> ORGANISM: Artificial
<220> FEATURE:
<223> OTHER INFORMATION: Primer

<400> SEQUENCE: 17
cgtaaataac taaatgatat cgagctcggt acc    33

<210> SEQ ID NO 18
<211> LENGTH: 41
<212> TYPE: DNA
<213> ORGANISM: Artificial
<220> FEATURE:
<223> OTHER INFORMATION: Primer

<400> SEQUENCE: 18
ccggggtacc gagctcgata tcatttagtt atttacgcat g    41

<210> SEQ ID NO 19
<211> LENGTH: 24
<212> TYPE: DNA
<213> ORGANISM: Artificial
<220> FEATURE:
<223> OTHER INFORMATION: Primer

<400> SEQUENCE: 19
tatcacgagg ccctttcgtc ttca    24

<210> SEQ ID NO 20
<211> LENGTH: 20
<212> TYPE: DNA
<213> ORGANISM: Artificial

```
<220> FEATURE:
<223> OTHER INFORMATION: Primer

<400> SEQUENCE: 20
ttcaccctct ccactgacag                                                   20

<210> SEQ ID NO 21
<211> LENGTH: 51
<212> TYPE: DNA
<213> ORGANISM: Artificial
<220> FEATURE:
<223> OTHER INFORMATION: Primer

<400> SEQUENCE: 21
gttaacaaca acaacaacca ccaccaccac caccactagg gctctatgag t                51

<210> SEQ ID NO 22
<211> LENGTH: 15
<212> TYPE: PRT
<213> ORGANISM: Homo sapiens

<400> SEQUENCE: 22

Asn Asn Asn Asn Asn His His His His His His Gly Ser Met Ser
 1               5                  10                  15

<210> SEQ ID NO 23
<211> LENGTH: 34
<212> TYPE: DNA
<213> ORGANISM: Homo sapiens

<400> SEQUENCE: 23
gcgagtaaag gagaagaact tttcactgga gttg                                   34

<210> SEQ ID NO 24
<211> LENGTH: 87
<212> TYPE: DNA
<213> ORGANISM: Homo sapiens

<400> SEQUENCE: 24
agaaaattaa gagaagatta aagactctgc ttagaaatag gccggtggc agcgcgagta        60 aaggagaaga acttttcact ggagttg                                           87

<210> SEQ ID NO 25
<211> LENGTH: 87
<212> TYPE: DNA
<213> ORGANISM: Homo sapiens

<400> SEQUENCE: 25
gtgcatctgc aatgttaatc atggcggagg aaaaggctcg ggccggtggc agcgcgagta       60
aaggagaaga acttttcact ggagttg                                           87

<210> SEQ ID NO 26
<211> LENGTH: 87
<212> TYPE: DNA
<213> ORGANISM: Homo sapiens

<400> SEQUENCE: 26
aggttgaagc caaggaagag tcggaggagt cggacgaggg ggccggtggc agcgcgagta       60
aaggagaaga acttttcact ggagttg                                           87

<210> SEQ ID NO 27
<211> LENGTH: 87
```

```
<212> TYPE: DNA
<213> ORGANISM: Homo sapiens
<220> FEATURE:
<221> NAME/KEY: misc_feature
<222> LOCATION: (18)..(18)
<223> OTHER INFORMATION: n is a, c, g, or t

<400> SEQUENCE: 27
tggaggagaa gaaagcantc atgggaccac tgaagaaagg ggccggtggc agcgcgagta      60
aaggagaaga acttttcact ggagttg                                         87

<210> SEQ ID NO 28
<211> LENGTH: 87
<212> TYPE: DNA
<213> ORGANISM: Homo sapiens

<400> SEQUENCE: 28
aaagtcgatt actaacagct gaagctgata aaaccattag ggccggtggc agcgcgagta      60
aaggagaaga acttttcact ggagttg                                         87

<210> SEQ ID NO 29
<211> LENGTH: 87
<212> TYPE: DNA
<213> ORGANISM: Homo sapiens

<400> SEQUENCE: 29
ctcgagcagc agcagaacgc agtttgcggg aacacatggg ggccggtggc agcgcgagta      60
aaggagaaga acttttcact ggagttg                                         87

<210> SEQ ID NO 30
<211> LENGTH: 87
<212> TYPE: DNA
<213> ORGANISM: Homo sapiens
<220> FEATURE:
<221> NAME/KEY: misc_feature
<222> LOCATION: (21)..(21)
<223> OTHER INFORMATION: n is a, c, g, or t

<400> SEQUENCE: 30
aggataagtg caagaaggct ncttccagct ccaaagcacg ggccggtggc agcgcgagta      60
aaggagaaga acttttcact ggagttg                                         87

<210> SEQ ID NO 31
<211> LENGTH: 87
<212> TYPE: DNA
<213> ORGANISM: Homo sapiens
<220> FEATURE:
<221> NAME/KEY: misc_feature
<222> LOCATION: (18)..(18)
<223> OTHER INFORMATION: n is a, c, g, or t

<400> SEQUENCE: 31
ctgaaaagaa gcctgcanaa aagaaaccta ctacagaggg ggccggtggc agcgcgagta      60
aaggagaaga acttttcact ggagttg                                         87

<210> SEQ ID NO 32
<211> LENGTH: 87
<212> TYPE: DNA
<213> ORGANISM: Homo sapiens

<400> SEQUENCE: 32
cagaggctgc ccacgggact gtaacccgtc actaccgcag ggccggtggc agcgcgagta      60
```

-continued

```
aaggagaaga acttttcact ggagttg                                               87

<210> SEQ ID NO 33
<211> LENGTH: 87
<212> TYPE: DNA
<213> ORGANISM: Homo sapiens

<400> SEQUENCE: 33
ttcttggacc aggtgctgga gaaatggtaa atgaagctgg ggccggtggc agcgcgagta          60
aaggagaaga acttttcact ggagttg                                               87

<210> SEQ ID NO 34
<211> LENGTH: 49
<212> TYPE: DNA
<213> ORGANISM: Homo sapiens

<400> SEQUENCE: 34
gggccggtgg caggcgcgag taaaggagaa gaacttttca ctggagttg                      49

<210> SEQ ID NO 35
<211> LENGTH: 18
<212> TYPE: PRT
<213> ORGANISM: Homo sapiens

<400> SEQUENCE: 35

Ala Ser Lys Gly Glu Glu Leu Phe Thr Gly Val Val Pro Ile Leu Val
 1               5                  10                  15

Glu Leu

<210> SEQ ID NO 36
<211> LENGTH: 69
<212> TYPE: PRT
<213> ORGANISM: Homo sapiens

<400> SEQUENCE: 36

Leu Met Ser Tyr Leu Ser Ala Cys Ser Ser Glu Val Pro His Gly Pro
 1               5                  10                  15

Val Asp Gln Lys Phe Gln Ser Ile Val Ile Gly Cys Ala Leu Glu Asp
                20                  25                  30

Gln Lys Lys Ile Lys Arg Arg Leu Lys Thr Leu Leu Arg Asn Arg Ala
            35                  40                  45

Gly Gly Ser Ala Ser Lys Gly Glu Glu Leu Phe Thr Gly Val Val Pro
        50                  55                  60

Ile Leu Val Glu Leu
65

<210> SEQ ID NO 37
<211> LENGTH: 69
<212> TYPE: PRT
<213> ORGANISM: Homo sapiens

<400> SEQUENCE: 37

Ile Arg Pro Ser Ser Leu Glu Gln Met Ala Lys Leu Lys Pro Ala Phe
 1               5                  10                  15

Ile Lys Pro Tyr Gly Thr Val Thr Ala Ala Asn Ser Ser Phe Leu Thr
                20                  25                  30

Asp Gly Ala Ser Ala Met Leu Ile Met Ala Glu Glu Lys Ala Arg Ala
            35                  40                  45

Gly Gly Ser Ala Ser Lys Gly Glu Glu Leu Phe Thr Gly Val Val Pro
        50                  55                  60
```

```
Ile Leu Val Glu Leu
 65

<210> SEQ ID NO 38
<211> LENGTH: 69
<212> TYPE: PRT
<213> ORGANISM: Homo sapiens

<400> SEQUENCE: 38

Lys Val Lys Ala Phe Leu Ala Asp Pro Ser Ala Phe Val Ala Ala
 1               5                  10                  15

Pro Val Ala Ala Ala Thr Thr Ala Ala Pro Ala Ala Ala Ala Pro
             20                  25                  30

Ala Lys Val Glu Ala Lys Glu Glu Ser Glu Glu Ser Asp Glu Gly Ala
         35                  40                  45

Gly Gly Ser Ala Ser Lys Gly Glu Glu Leu Phe Thr Gly Val Val Pro
     50                  55                  60

Ile Leu Val Glu Leu
 65

<210> SEQ ID NO 39
<211> LENGTH: 69
<212> TYPE: PRT
<213> ORGANISM: Homo sapiens
<220> FEATURE:
<221> NAME/KEY: misc_feature
<222> LOCATION: (40)..(40)
<223> OTHER INFORMATION: Xaa can be any naturally occurring amino acid

<400> SEQUENCE: 39

Lys Ser Leu Leu Val Gln Thr Lys Arg Arg Ala Leu Glu Lys Ile Asp
 1               5                  10                  15

Leu Lys Phe Ile Asp Thr Thr Ser Lys Phe Gly His Gly Arg Phe Gln
             20                  25                  30

Thr Met Glu Glu Lys Lys Ala Xaa Met Gly Pro Leu Lys Lys Gly Ala
         35                  40                  45

Gly Gly Ser Ala Ser Lys Gly Glu Glu Leu Phe Thr Gly Val Val Pro
     50                  55                  60

Ile Leu Val Glu Leu
 65

<210> SEQ ID NO 40
<211> LENGTH: 69
<212> TYPE: PRT
<213> ORGANISM: Homo sapiens

<400> SEQUENCE: 40

Trp Arg Thr Gly Tyr Asn Phe Gln Arg Val His Ala Ala Val Gln Pro
 1               5                  10                  15

Gly Ser Leu Asp Ser Glu Ser Gly Ile Phe Ala Cys Ala Phe Asp Gln
             20                  25                  30

Ser Glu Ser Arg Leu Leu Thr Ala Glu Ala Asp Lys Thr Ile Arg Ala
         35                  40                  45

Gly Gly Ser Ala Ser Lys Gly Glu Glu Leu Phe Thr Gly Val Val Pro
     50                  55                  60

Ile Leu Val Glu Leu
 65

<210> SEQ ID NO 41
```

```
<211> LENGTH: 69
<212> TYPE: PRT
<213> ORGANISM: Homo sapiens

<400> SEQUENCE: 41

Ser Arg Glu Gln Lys Ala Lys Gln Glu Arg Glu Lys Glu Leu Ala Lys
1               5                   10                  15

Val Thr Ile Lys Lys Glu Asp Leu Glu Leu Ile Met Thr Glu Met Glu
            20                  25                  30

Ile Ser Arg Ala Ala Ala Glu Arg Ser Leu Arg Glu His Met Gly Ala
        35                  40                  45

Gly Gly Ser Ala Ser Lys Gly Glu Glu Leu Phe Thr Gly Val Val Pro
    50                  55                  60

Ile Leu Val Glu Leu
65

<210> SEQ ID NO 42
<211> LENGTH: 69
<212> TYPE: PRT
<213> ORGANISM: Homo sapiens
<220> FEATURE:
<221> NAME/KEY: misc_feature
<222> LOCATION: (41)..(41)
<223> OTHER INFORMATION: Xaa can be any naturally occurring amino acid

<400> SEQUENCE: 42

Asp Ser Lys Lys Pro Ala Asp Gln Asp Pro Ile Asp Ala Leu Ser
1               5                   10                  15

Gly Asp Leu Asp Ser Cys Pro Ser Thr Thr Glu Thr Ser Gln Asn Thr
            20                  25                  30

Ala Lys Asp Lys Cys Lys Lys Ala Xaa Ser Ser Ser Lys Ala Arg Ala
        35                  40                  45

Gly Gly Ser Ala Ser Lys Gly Glu Glu Leu Phe Thr Gly Val Val Pro
    50                  55                  60

Ile Leu Val Glu Leu
65

<210> SEQ ID NO 43
<211> LENGTH: 69
<212> TYPE: PRT
<213> ORGANISM: Homo sapiens
<220> FEATURE:
<221> NAME/KEY: misc_feature
<222> LOCATION: (40)..(40)
<223> OTHER INFORMATION: Xaa can be any naturally occurring amino acid

<400> SEQUENCE: 43

Pro Val Val Gly Lys Lys Gly Lys Lys Ala Ala Val Gly Val Lys Lys
1               5                   10                  15

Gln Lys Lys Pro Leu Val Gly Lys Ala Ala Ala Thr Lys Lys Pro
            20                  25                  30

Ala Pro Glu Lys Lys Pro Ala Xaa Lys Lys Pro Thr Thr Glu Gly Ala
        35                  40                  45

Gly Gly Ser Ala Ser Lys Gly Glu Glu Leu Phe Thr Gly Val Val Pro
    50                  55                  60

Ile Leu Val Glu Leu
65

<210> SEQ ID NO 44
<211> LENGTH: 69
<212> TYPE: PRT
```

-continued

```
<213> ORGANISM: Homo sapiens

<400> SEQUENCE: 44

Tyr Asp Gly Asp Val Gln Ser Asp Ser Val Ala Gln Gly Tyr Gly Ser
1               5                   10                  15

Leu Gly Met Met Thr Ser Val Leu Val Cys Pro Asp Gly Lys Thr Val
            20                  25                  30

Glu Ala Glu Ala Ala His Gly Thr Val Thr Arg His Tyr Arg Arg Ala
        35                  40                  45

Gly Gly Ser Ala Ser Lys Gly Glu Glu Leu Phe Thr Gly Val Val Pro
    50                  55                  60

Ile Leu Val Glu Leu
65

<210> SEQ ID NO 45
<211> LENGTH: 69
<212> TYPE: PRT
<213> ORGANISM: Homo sapiens

<400> SEQUENCE: 45

Pro Phe Ala Ala Asn Ser Arg Ala Lys Thr Asn Ala Asp Thr Asp Gly
1               5                   10                  15

Met Val Lys Ile Leu Gly Gln Lys Ser Thr Asp Arg Val Leu Gly Ala
            20                  25                  30

His Ile Leu Gly Pro Gly Ala Gly Glu Met Val Asn Glu Ala Gly Ala
        35                  40                  45

Gly Gly Ser Ala Ser Lys Gly Glu Glu Leu Phe Thr Gly Val Val Pro
    50                  55                  60

Ile Leu Val Glu Leu
65

<210> SEQ ID NO 46
<211> LENGTH: 22
<212> TYPE: PRT
<213> ORGANISM: Homo sapiens

<400> SEQUENCE: 46

Ala Gly Gly Ser Ala Ser Lys Gly Glu Glu Leu Phe Thr Gly Val Val
1               5                   10                  15

Pro Ile Leu Val Glu Leu
            20
```